US008449881B2

United States Patent
Leu et al.

(10) Patent No.: US 8,449,881 B2
(45) Date of Patent: May 28, 2013

(54) ANTI-α-ENOLASE I ANTIBODIES FOR DIAGNOSIS AND TREATMENT OF α-ENOLASE I-ASSOCIATED DISEASES

(75) Inventors: Sy-Jye Leu, Taipei (TW); Yi-Yuan Yang, Taipei (TW); Neng-Yao Shih, Miaoli County (TW); I-Jen Huang, Tainan (TW); Ko-Jiunn Liu, Miaoli County (TW); Yu-Ching Lee, Taipei (TW); Yung-Leun Shih, Taipei (TW); Yu-Jia Chang, Taipei (TW); Bor-Yu Tsai, Taipei (TW); Yuan-Soon Ho, Taipei (TW)

(73) Assignee: Taipei Medical University, Taipei (TW)

( * ) Notice: Subject to any disclaimer, the term of this patent is extended or adjusted under 35 U.S.C. 154(b) by 447 days.

(21) Appl. No.: 12/695,627

(22) Filed: Jan. 28, 2010

(65) Prior Publication Data

US 2011/0182907 A1 Jul. 28, 2011

(51) Int. Cl.
 *A61K 39/395* (2006.01)
(52) U.S. Cl.
 USPC ..................................... 424/130.1; 530/387.1
(58) Field of Classification Search
 USPC ...................................................... 424/130.1
 See application file for complete search history.

(56) References Cited

U.S. PATENT DOCUMENTS 5,367,054 A * 11/1994 Lee ................................ 530/359
7,645,453 B2 * 1/2010 Shih et al. .................. 424/184.1

FOREIGN PATENT DOCUMENTS

WO WO/2010/032899 * 3/2010

OTHER PUBLICATIONS

Antikainen et al., 2007, FEMS Immunol Med Microbiol 51, 526-534.
Chang, et al., 2006, Clin Cancer Res 12, 5746-5754.
Lee et al., 2003, Arthritis Rheum 48, 2025-2035.
Redlitz et al., 1995, Eur J Biochem 227, 407-415.
Peebles et al., 2003, Carcinogenesis 24, 651-657.
Satoshi Ito, 2007, Cancer Science 98, 499-505.
Wu et al., 2002, Clin Exp Metastasis 19, 319-326.
Zhang et al., 2000, J Surg Res 93, 108-119.
Altenberg and Greulich, 2004, Genomics 84, 1014-1020.
Bogdanos et al., 2004, J Autoimmune Dis 1, 4.
Gitlits et al., 2001, J Investig Med 49, 138-145.
Jiang et al., 1997, Cancer Res 57, 5328-5335.
Kinloch et al., 2005, Arthritis Res Ther 7, R1421-1429.
Saulot et al., 2002, Arthritis Rheum 46, 1196-1201.

* cited by examiner

*Primary Examiner* — Laura B Goddard
*Assistant Examiner* — Meera Natarajan
(74) *Attorney, Agent, or Firm* — WPAT, P.C.; Anthony King

(57) ABSTRACT

The invention relates to antibodies against α-enolase I, their pharmaceutical compositions and diagnosis and treatment uses. Particularly, the invention provides polyclonal anti-α-enolase I antibodies and monoclonal single-chain variable fragment (scFv) anti-α-enolase antibodies, pharmaceutical compositions containing the same and their uses in uses in diagnosis and treatment of cancers, autoimmune disorders, ischemia and bacterial infection.

10 Claims, 9 Drawing Sheets

(4 of 9 Drawing Sheet(s) Filed in Color)

Germline VL: SEQ ID NO:49; EnL1 VL: SEQ ID NO: 31; EnL2 VL: SEQ ID NO: 32; EnL3 VL: SEQ ID NO: 33; EnL4 VL: SEQ ID NO: 34; EnL5 VL: SEQ ID NO: 35

Germline VH: SEQ ID NO:50; EnL1 VH: SEQ ID NO: 36; EnL2 VH: SEQ ID NO: 37; EnL3 VH: SEQ ID NO: 38; EnL4 VH: SEQ ID NO: 39; EnL5 VH: SEQ ID NO: 40

US 8,449,881 B2

ANTI-α-ENOLASE I ANTIBODIES FOR DIAGNOSIS AND TREATMENT OF α-ENOLASE I-ASSOCIATED DISEASES

FIELD OF THE INVENTION

The invention relates to antibodies against α-enolase I, their pharmaceutical compositions and diagnosis and treatment uses. Particularly, the invention provides polyclonal anti-α-enolase I antibodies and monoclonal single-chain variable fragment (scFv) anti-α-enolase antibodies, pharmaceutical compositions containing the same and their uses in uses in diagnosis and treatment of cancers, autoimmune disorders, ischemia and bacterial infection.

BACKGROUND OF THE INVENTION

Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. The identification of such tumor-associated cell surface antigen polypeptides has given rise to the ability to specifically target cancer cells for destruction via antibody-based therapies. In attempts to discover effective cellular targets for cancer therapy or detection, researchers have sought to identify polypeptides that are specifically overexpressed on the surface of a particular type of cancer cell as compared to on one or more normal non-cancerous cell(s). In other attempts to discover effective cellular targets for cancer therapy, researchers have sought to identify polypeptides that are produced and secreted by a particular type of cancer cell at an expression level that is higher than that produced and secreted by one or more normal non-cancerous cell(s). Despite the above identified advances in mammalian cancer therapy, there is a great need for additional diagnostic and therapeutic agents capable of detecting the presence of tumor in a mammal and for treating cancer, respectively.

Enolase was originally characterized as an enzyme involved in glycolytic metabolism catalyzing the conversion of 2-phosphoglycerate into phosphoenolpyruvate. In mammals there are three isoforms of enolase, called α-ENO1, β-ENO3 and γ-ENO2. The α-enolase is a major from of enolase present in the early stages of embryonic development, being expressed ubiquitously in various types of tissue, whereas γ-ENO2 and β-ENO3 are exclusively found in neuron and muscle cells (Antikainen et al., 2007, FEMS Immunol Med Microbiol 51, 526-534; Chang, et al., 2006, Clin Cancer Res 12, 5746-5754). The information regarding nucleic acid and amino acid sequences of α-enolase can be obtained from NCBI website. It was reported that α-enolase is a multifunctional protein which exhibits enzymatic, structural, and receptor functions (Chang, et al., 2006, Clin Cancer Res 12, 5746-5754; Lee et al., 2003, Arthritis Rheum 48, 2025-2035). In addition to its glycolytic function, α-enolase has been found to play an important role in several biological and pathophysiological processes. Particularly, α-enolase is considered to play important roles in tumorigenesis. This protein was found on the cell surface functioning as one of the plasminogen receptors which may play a role in tumor invasion (Redlitz et al., 1995, Eur J Biochem 227, 407-415). Up-regulation of α-enolase has been reported in several highly tumorigenic or metastatic cell lines (Chang et al., 2006, Clin Cancer Res 12, 5746-5754; Peebles et al., 2003, Carcinogenesis 24, 651-657; Satoshi Ito, 2007, Cancer Science 98, 499-505; Wu et al., 2002, Clin Exp Metastasis 19, 319-326; Zhang et al., 2000, J Surg Res 93, 108-119). α-enolase over-expression was correlated with tumorigenicity on several types of cancer which suggest its pathophysiologic role in cancer formation (Altenberg and Greulich, 2004, Genomics 84, 1014-1020). Furthermore, an autoantigen of α-enolase was identified in non-small cell lung cancer and its overexpression was highly correlated with poor survival outcomes (Chang et al., 2006, Clin Cancer Res 12, 5746-5754). In addition to its roles in cancer, α-enolase has been implicated in numerous diseases, including autoimmune disorders, ischemia and bacterial infection. (Antikainen et al., 2007, FEMS Immunol Med Microbiol 51, 526-534; Bogdanos et al., 2004, J Autoimmune Dis 1, 4; Gitlits et al., 2001, J Investig Med 49, 138-145; Jiang et al., 1997, Cancer Res 57, 5328-5335; Kinloch et al., 2005, Arthritis Res Ther 7, R1421-1429; Saulot et al., 2002, Arthritis Rheum 46, 1196-1201).

Therefore, α-enolase is a potential target for therapeutics of treating or preventing cancer development or for detection of cancer. There remains a need for detecting, treating, preventing, and reversing the development of cancers.

SUMMARY OF THE INVENTION

One object of the invention is to provide an avian-derived anti-α-enolase I polyclonal antibody which specifically bind to α-enolase I.

Another object of the invention is to provide a purified monoclonal antibody, or antigen-binding fragment thereof, comprising a heavy chain immunoglobulin variable domain and a light chain immunoglobulin variable domain that binds to α-enolase I, wherein the light chain immunoglobulin variable domain comprises the amino acid sequence of: (i) SGGSGSYG (SEQ ID NO: 1), SGGSSSYGYG (SEQ ID NO: 2), SGSSGSYG (SEQ ID NO: 3), SGGSSSYGYS (SEQ ID NO: 4) or SGSSGYGYG (SEQ ID NO: 5) in CDR1, (ii) ANTNRPS (SEQ ID NO: 6), NDNQRPS (SEQ ID NO: 7), RDDKRPS (SEQ ID NO: 8), SNNQRPS (SEQ ID NO: 9) or SNDKRPS (SEQ ID NO: 10) in CDR2, and (iii) GGYDSSAGI (SEQ ID NO: 11), GSGDSSTGM (SEQ ID NO: 12), GSGESSTNNGI (SEQ ID NO: 13), GSMDSSNSGV (SEQ ID NO: 14) or GGYDSSASYVGI (SEQ ID NO: 15) in CDR3; and wherein the heavy chain immunoglobulin variable domain comprises the amino acid sequence of: (i) SFNMF (SEQ ID NO: 16), SHDMG (SEQ ID NO: 17), DYCVQ (SEQ ID NO: 18), SFYMF (SEQ ID NO: 19) or SYAMH (SEQ ID NO: 20) in CDR1, (ii) GINNAGSTTNHGAAVKG (SEQ ID NO: 21), GIENAAGIGTFYGAAVKG (SEQ ID NO: 22), AISNTGRYTGYGSAVKG (SEQ ID NO: 23), GISGDGRYTGYGAAVDG (SEQ ID NO: 24) or GISRDGGSSTRYYGAAVKG (SEQ ID NO: 25) in CDR2, and (iii) SPGGIDGIDG (SEQ ID NO: 26), GADTGGWPAANIDA (SEQ ID NO: 27), DGCAGCCGSYYIDG (SEQ ID NO: 28), ESGSGCCNGDNIDA (SEQ ID NO: 29) or DSDNGGYYCDDIDA (SEQ ID NO: 30) in CDR3.

A further object of the invention is to provide a pharmaceutical composition, comprising the polyclonal antibody of the invention and a pharmaceutically acceptable carrier.

Another further object of the invention is to provide a method of treating or preventing an α-enolase I-associated disorder, comprising administrating therapeutic effective amount of the polyclonal antibody or monoclonal antibody of the invention.

Another further object of the invention is to provide an in vitro diagnostic method for detecting the presence of an α-enolase I in a sample, comprising: (i) contacting a sample with anti-α-enolase I antibody of the invention; and (ii) detecting formation of a complex between the α-enolase I antibody and the sample.

Another further object of the invention is to provide a kit for the detection of the presence of an α-enolase I in a sample, comprising an anti-α-enolase I antibody of the invention, or fragment thereof, and optionally an informational material.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
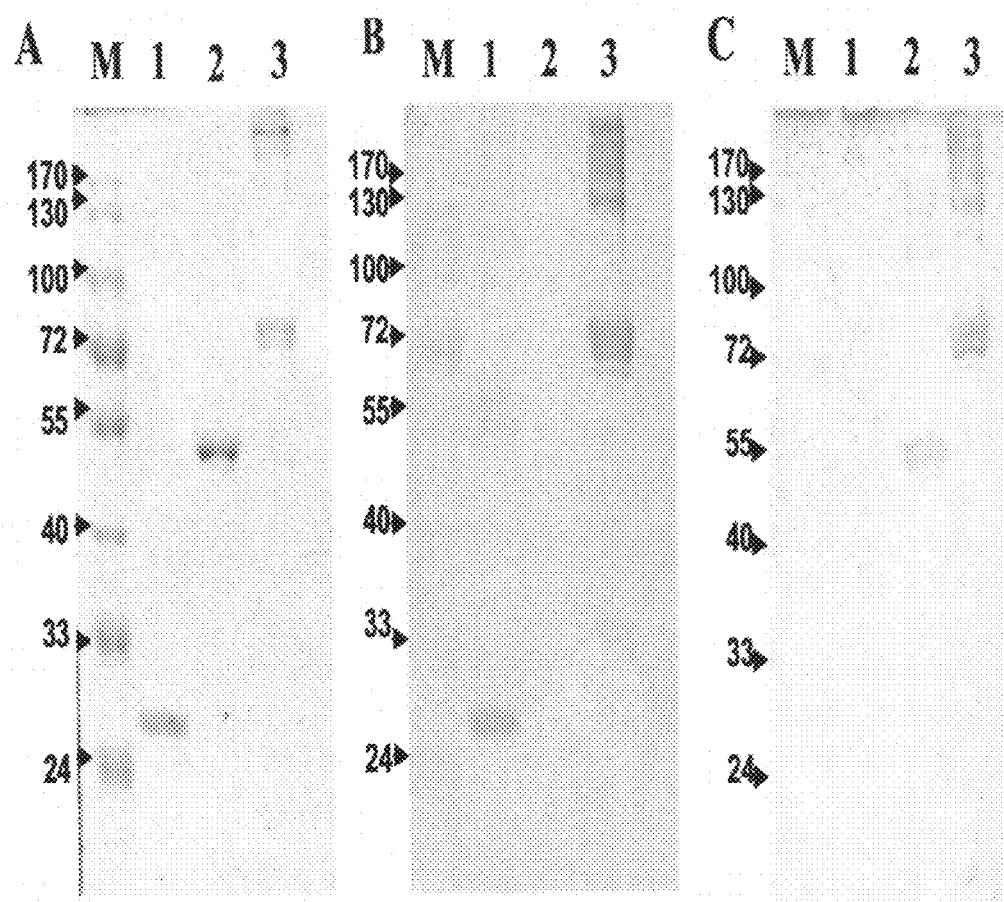
FIG. 1 is characterization of recombinant α-enolase and polyclonal anti-α-enolase IgY antibodies. Samples in each panel are protein markers (lane M), purified GST (lane 1), purified α-enolase (lane 2), and purified GST-α-enolase fusion protein (lane 3). Purified proteins visualized by Coomassie blue staining (panel A) were blotted onto nitrocellulose paper and probed with anti-GST antibodies (panel B) or sera from 4th-immunized chicken (panel C). The molecular weight of recombinant α-enolase protein is about 48 kD.

The invention generates and characterizes polyclonal anti-α-enolase I antibodies from immunized chickens and monoclonal single-chain variable fragment (scFv) anti-α-enolase I antibodies by phage display system. These antibodies may be helpful in the development of molecular diagnostic and therapeutic agents for cancers, autoimmune disorders, ischemia and bacterial infection.

Definitions

It is to be noted that the term "a" or "an" entity refers to one or more of that entity; for example, "an anti-enolase I antibody," is understood to represent one or more anti-enolase I antibodies. As such, the terms "a" (or "an"), "one or more," and "at least one" can be used interchangeably herein.

As used herein, the term "isolated" or "purified" means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes.

As used herein, the term "antibodies" refers to complete antibodies or antibody fragments capable of binding to a selected target. Included are Fv, scFv, Fab' and F(ab')2, monoclonal and polyclonal antibodies, engineered antibodies (including chimeric, CDR-grafted and humanized, fully human antibodies, and artificially selected antibodies), and synthetic or semi-synthetic antibodies produced using phage display or alternative techniques. Small fragments, such as Fv and scFv, possess advantageous properties for diagnostic and therapeutic applications on account of their small size and consequent superior tissue distribution.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to an α-enolase. For example, antibody fragments capable of binding to α-enolase or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method known in the art, or may be made by recombinant DNA methods such as described in U.S. Pat. No. 4,816,567. The "monoclonal antibodies" may also be isolated from phage libraries generated using the techniques described in McCafferty et al., Nature, 348:552-554 (1990), for example.

The term "specifically binds" generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope.

The terms "treating," "treatment," and "therapy" as used herein refer to curative therapy, prophylactic therapy, and preventative therapy.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, blastoma, gastrointestinal cancer, renal cancer, pancreatic cancer, glioblastoma, neuroblastoma, cervical cancer, ovarian cancer, liver cancer, stomach cancer, bladder cancer, hepatoma, breast cancer, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

The term "subject" or "individual" or "animal" or "patient" or "mammal," is mean any subject, particularly a mammalian subject, for whom diagnosis or therapy is desired. Mammalian subjects include humans, domestic animals, farm animals, and zoo, sports, or pet animals such as dogs, cats, guinea pigs, rabbits, rats, mice, horses, cattle, cows, and so on.

Antibodies

The invention relates to antibodies, antigen-binding antibody fragments thereof, and variants of the antibodies and fragments, that specifically bind to α-enolase I polypeptide. These antibodies can be, for example, polyclonal or monoclonal antibodies. More preferred are monoclonal antibodies. Still more preferred are chimeric or humanized antibodies, and still more preferred are human antibodies.

Polyclonal Antibodies

In one aspect, the invention provides an avian-derived anti-α-enolase I polyclonal antibody which specifically bind to α-enolase I. In one embodiment of the invention, the avian is chicken and the polyclonal antibody is polyclonal anti-α-enolase I IgY antibody. Preferably, the polyclonal antibody is anti-α-enolase I chicken IgY antibody.

The production of the polyclonal antibody is known in the art. First, avian species (e.g. chickens, ducks, turkeys, and the like) are immunized with multiple injections of human α-enolase I polypeptide to initiate an immunogenic response in the avian. After a suitable amount of time has elapsed to establish a high titer of anti-α-enolase I antibodies within the avian, serum or eggs are collected from the α-enolase I-immunized avian.

The serum and egg yolks from the immunized birds contain a wide variety of antibodies specific for any number of antigens from natural exposure. The next step of the process is to isolate the IgY fraction of immunoglobulim (which fraction is known to contain α-enolase I-specific antibodies) from the serum or egg yolks. This can be accomplished with the egg yolks by utilizing a commercial product, for instance, Promega Corporation's EGGstract® IgY Purification System (Promega Corporation, Madison, Wis. U.S.A.) and HiTrap™ IgY Purification HP Column (GE Healthcare, U.S.A.). There also are a number of other methods for isolating immunoglobulins from egg yolks, such as other sequential precipitation methods, which are well known to those skilled in the art. (See, for instance, Scopes, R. K. "Protein Purification: Principles and Practice", Springer-Verlag New York, 1994), which is incorporated herein by reference for its teaching of protein purification methods). The conventional method of protein isolation, which is completely satisfactory to practice the present invention, is to "salt out" the protein fractions by precipitation of the proteins from a salt solution. The IgY polyclonal antibodies from the serum of the avian can be isolated using, for instance, chromatographical methods. Again, there are a number of methods well known to those skilled in the art for isolating immunoglobulins from serum or egg yolk samples.

The next step of the process is to separate the α-enolase I-specific polyclonal antibodies (pAbs) from the non-specific antibodies within the IgY fraction. To accomplish this, the isolated IgY fraction is applied to an affinity column constructed by coupling α-enolase I to a resin to create an affinity matrix. This enzyme-bound matrix will capture only those antibodies within the IgY fraction which are specific for α-enolase I. The non-specific polyclonal antibodies within the IgY fraction are removed from the column by multiple washings with a simple saline buffer solution. This leaves the matrix containing only those polyclonal antibodies which are specific for α-enolase I.

Monoclonal Antibodies

In another aspect, the invention provides a purified monoclonal antibody, or antigen-binding fragment thereof, comprising a heavy chain immunoglobulin variable domain and a light chain immunoglobulin variable domain that binds to α-enolase I, wherein the light chain immunoglobulin variable domain comprises the amino acid sequence of: (i) SGGSGSYG (SEQ ID NO: 1), SGGSSSYGYG (SEQ ID NO: 2), SGSSGSYG (SEQ ID NO: 3), SGGSSSYGYS (SEQ ID NO: 4) or SGSSGYGYG (SEQ ID NO: 5) in CDR1, (ii) ANTNRPS (SEQ ID NO: 6), NDNQRPS (SEQ ID NO: 7), RDDKRPS (SEQ ID NO: 8), SNNQRPS (SEQ ID NO: 9) or SNDKRPS (SEQ ID NO: 10) in CDR2, and (iii) GGYDSSAGI (SEQ ID NO: 11), GSGDSSTGM (SEQ ID NO: 12), GSGESSTNNGI (SEQ ID NO: 13), GSMDSSNSGV (SEQ ID NO: 14) or GGYDSSASYVGI (SEQ ID NO: 15) in CDR3; and wherein the heavy chain immunoglobulin variable domain comprises the amino acid sequence of: (i) SFNMF (SEQ ID NO: 16), SHDMG (SEQ ID NO: 17), DYCVQ (SEQ ID NO: 18), SFYMF (SEQ ID NO: 19) or SYAMH (SEQ ID NO: 20) in CDR1, (ii) GINNAGSTTNHGAAVKG (SEQ ID NO: 21), GIENAAGIGTFYGAAVKG (SEQ ID NO: 22), AISNTGRYTGYGSAVKG (SEQ ID NO: 23), GISGDGRYTGYGAAVDG (SEQ ID NO: 24) or GISRDGGSSTRYYGAAVKG (SEQ ID NO: 25) in CDR2, and (iii) SPGGIDGIDG (SEQ ID NO: 26), GADTGGWPAANIDA (SEQ ID NO: 27), DGCAGCCGSYYIDG (SEQ ID NO: 28), ESGSGCCNGDNIDA (SEQ ID NO: 29) or DSDNGGYYCDDIDA (SEQ ID NO: 30) in CDR3.

In one embodiment, the purified monoclonal antibody or antigen-binding fragment thereof of the invention comprises framework regions from VH and VL FR1, FR2, FR3 and FR4 framework regions encoded by germline gene sequence of chicken immunoglobulin (please refer to www.ncbi.nlm.nih.gov/nuccore/16902088 and http://www.ncbi.nlm.nih.gov/sites/entrez?cmd=Retrieve&db=protein&dopt=GenPept&RID=MS2P2YSH012&log%24=prottop&blast_rank=1&list_uids=104726 for VL and VH, respectively) or an amino acid sequence at least 85% identical to the VH and VL FR1, FR2 and FR3 framework regions encoded by the germline gene sequence of chicken immunoglobulin. Preferably, the purified antibody or antigen-binding fragment thereof comprises framework regions from an amino acid sequence at least 87%, 88%, 89%, 90%, 91%, 92%, 93%, 94%, 95%, 97%, 98%, or 99% identical to the VH and VL FR1, FR2 and FR3 framework regions encoded by the germline gene sequence of chicken immunoglobulin. The VH and VL domains of the monoclonal antibodies of the invention, in certain embodiments, can be germlined, i.e., the framework regions (FRs) of these domains may be changed using conventional molecular biology techniques to match human germline genes or the consensus amino acid sequences of human germline gene products, at one or more positions (e.g., at least 70%, 80%, 85%, 87%, 88%, 89%, 90%, 91%, 92%, 93%, 94% or 95%, 97%, 98%, or 99% of framework positions). In other embodiments, the framework sequences remain diverged from the germline.

In one embodiment, the purified monoclonal antibody or antigen-binding fragment thereof of the invention comprises VL complementarity determining region having an amino acid sequence selected from the group consisting of the following amino acid sequences: i) SEQ ID NO:1 in CDR1, SEQ ID NO: 6 in CDR2 and SEQ ID NO: 11 in CDR3; ii) SEQ ID NO:2 in CDR1, SEQ ID NO: 7 in CDR 2 and SEQ ID NO: 12 in CDR3; iii) SEQ ID NO: 3 in CDR1, SEQ ID NO: 8 in CDR 2 and SEQ ID NO: 13 in CDR3; iv) SEQ ID NO: 4 in CDR 1, SEQ ID NO: 9 in CDR 2 and SEQ ID NO: 14 in CDR3 and v) SEQ ID NO: 5 in CDR1, SEQ ID NO: 10 in CDR2 and SEQ ID NO: 15 in CDR3 and VH complementarity determining region having an amino acid sequence selected from the group consisting of the following amino acid sequences: i) SEQ ID NO: 16 in CDR1, SEQ ID NO: 21 in CDR2 and SEQ ID NO: 26 in CDR3; ii) SEQ ID NO: 17 in CDR1, SEQ ID NO: 22 in CDR2 and SEQ ID NO: 27 in CDR3; iii) SEQ ID NO: 18 in CDR1, SEQ ID NO: 23 in CDR2 and SEQ ID NO: 28 in CDR3; iv) SEQ ID NO: 19 in CDR1, SEQ ID NO: 24 in CDR2 and SEQ ID NO: 29 in CDR3 and v) SEQ ID NO: 20 in CDR1, SEQ ID NO: 25 in CDR2 and SEQ ID NO: 30 in CDR3. Preferably, the VL complementarity determining region having an amino acid sequence mentioned in ii) or v) and VH complementarity determining region having an amino acid sequence mentioned in ii) or v).

In yet another embodiment, the purified monoclonal antibody or antigen-binding fragment thereof of the invention comprises the light chain immunoglobulin variable domain having an amino acid sequence selected from the group consisting of SEQ ID NOs: 31-35 and the heavy chain immunoglobulin variable domain having an amino acid sequence selected from the group consisting of 36-40.

In one embodiment, an antibody or fragment thereof has CDR sequences that differ only insubstantially from those of the antibodies described herein. Insubstantial differences include minor amino acid changes, such as substitutions of 1 or 2 out of any of typically 5-7 amino acids in the sequence of a CDR, e.g., a Chothia or Kabat CDR. Typically an amino acid is substituted by a related amino acid having similar charge, hydrophobic, or stereochemical characteristics. Such substitutions would be within the ordinary skills of an artisan. Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J. Immunol. 147:2657-62; Morgan et al. (1995) Immunology 86:319-24), or changing the species from which the constant region is derived.

The monoclonal antibodies or antigen binding fragments thereof the invention can be obtained by phage display techniques. Phage display involves the localization of peptides as terminal fusions to the coat proteins, e.g., pIII, pIIV of bacteriophage particles. See Scott, J. K. and G. P. Smith (1990) Science 249(4967):386-390; and Lowman, H. B., et al. (1991) Biochem. 30(45):10832-10838. Generally, polypeptides with a specific function of binding are isolated by incubating with a target, washing away non-binding phage, eluting the bound phage, and then re-amplifying the phage population by infecting a fresh culture of bacteria. Other display formats and methodologies include mRNA display, ribosome or polysome display, eukaryotic virus display, and bacterial, yeast, and mammalian cell surface display. See Mattheakis, L. C., et al. (1994) PNAS USA 91(19): 9022-9026; W; ilson, D. S., et al. (2001) PNAS USA 98(7):3750-3755; Shusta, E. V., et al. (1999) Curt Opin. Biotech. 10(2): 117-122; and Boder, E. T. and K. D. Wittrup (1997) Nature Biotech. 15(6):553-557. A variety of alternative display technologies have been developed and reported for display on the surface of a microorganism and pursued as a general strategy for isolating protein binding peptides without reported successes. See Maurer, J., et al. (1997) J. Bacteriol. 179(3):794-804; Samuelson, P., et al. (1995) J. Bacteriol. 177(6):1470-1476; Robert, A., et al. (1996) FEBS Letters 390(3): 327-333; Stathopoulos, C., et al. (1996) Appl. Microbiol. & Biotech. 45(1-2): 112-119; Georgiou, G., et al., (1996) Protein Engineering 9(2): 239-247; Haddad, D., et al., (1995) FEMS Immunol. & Medical Microbiol. 12(3-4):175-186; Pallesen, L., et al., (1995) Microbiol. 141(Pt 11): 2839-2848, Xu, Z. and S. Y. Lee (1999) Appl. Environ. Microbiol. 65(11):5142-5147; Wernerus, H. and S. Stahl (2002) FEMS Microbiol. Lett. 212(1): 47-54; and Westerlund-Wikstrom, B. (2000) Int. J. Med. Microbiol. 290(3):223-230.

The polyclonal or monoclonal antibodies described herein may also be tagged with a detectable or functional label. Detectable labels include radiolabels such as $^{131}$I or 99Tc, which may be attached to antibodies described herein using conventional chemistry known in the art. Labels also include enzyme labels such as horseradish peroxidase or alkaline phosphatase. Labels further include chemical moieties such as biotin, which may be detected via binding to a specific cognate detectable moiety, e.g., labeled avidin.

The binding characteristics of an antibody disclosed herein may be measured by any suitable methods, including the following methods: Biacore analysis, Enzyme Linked Immunosorbent Assay (ELISA), x-ray crystallography, sequence analysis and scanning mutagenesis, and other methods that are well known in the art.

Pharmaceutical Composition of the Invention

Anti-α-enolase I antibodies can be incorporated into a pharmaceutical composition, e.g., by combination with a pharmaceutically acceptable carrier. Such a composition may also contain, e.g., various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier can depend on the route of administration.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing an exemplary method of treatment or use described herein, a therapeutically effective amount of antibody that binds to α-enolase I and interferes with the formation of a functional α-enolase I signaling complex (and, e.g., neutralizes or inhibits one or more α-enolase I associated activities), can be administered to a subject, e.g., mammal (e.g., a human). An antibody may be administered in accordance with the methods described either alone or in combination with other therapies. When coadministered with one or more agents, the antibody may be administered either simultaneously with the second agent, or separately, e.g., sequentially. If administered separately, e.g., sequentially, the attending physician will decide on the appropriate sequence of administering the antibody in combination with other agents.

Administration of a pharmaceutical composition (e.g., a pharmaceutical composition containing an antibody that binds to α-enolase I) can be carried out in a variety of conventional ways, such as oral ingestion, inhalation, or cutaneous, subcutaneous, or intravenous injection. Subcutaneous administration to the patient is preferred.

When a therapeutically effective amount of an antibody that binds to α-enolase I and interferes with the formation of a functional α-enolase I signaling complex is administered orally, the binding agent will be in the form of a tablet, capsule, powder, solution or elixir. When administered in tablet form, a pharmaceutical composition may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol.

When a therapeutically effective amount of an antibody that binds to α-enolase I is administered by intravenous, cutaneous, or subcutaneous injection, the binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. A pharmaceutical composition may also contain stabilizers, preservatives, buffers, antioxidants, or other additive known to those of skill in the art.

The amount of an antibody in the pharmaceutical composition can depend upon the nature and severity of the condition being treated, and on the nature of prior treatments that the patient has undergone. Ultimately, the attending physician will decide the amount of antibody with which to treat each individual patient. Initially, the attending physician will administer low doses of antibody and observe the patient's response. Larger doses of antibody may be administered until the optimal therapeutic effect is obtained for the patient, and at that point the dosage is not generally increased further. For example, doses in the range of 0.1-50 mg/kg, 0.5-50 mg/kg, 1-100 mg/kg, 0.5-25 mg/kg, 0.1-15 mg/kg, or 1-8 mg/kg of body weight can be administered.

Therapeutic and Prophylactic Uses of Anti-α-Enolase I Antibodies

The antibodies of the invention may be used to treat an α-enolase I-associated disorder, e.g., a disorder chosen from one or more of: cancers, autoimmune disorders, ischemia and bacterial infection.

α-enolase I and its receptors may be involved in the development of at least some types of cancer, e.g., a cancer derived from hematopoietic cells or a cancer derived from lung cancer. Preferable, the cancer is lung cancer, breast cancer, anal cancer, bladder cancer, bone cancer, bowel cancer, brain tumours, kidney cancer, leukemia, liver cancer, pancreatic cancer, prostate cancer, rectal cancer. More preferably, the lung cancer is non-small-cell lung cancer. A cancer refers to one or more cells that has a loss of responsiveness to normal growth controls, and typically proliferates with reduced regulation relative to a corresponding normal cell.

Diagnostic Uses of Anti-α-Enolase I Antibodies

In another aspect, the present invention provides a diagnostic method for detecting the presence of a α-enolase I, in vitro (e.g., a biological sample, such as tissue, biopsy). The method includes: (i) contacting a sample with anti-α-enolase I antibody of the invention; and (ii) detecting formation of a complex between the α-enolase I antibody and the sample.

The method can also include contacting a reference sample (e.g., a control sample) with the ligand, and determining the extent of formation of the complex between the ligand and the sample relative to the same for the reference sample. A change, e.g., a statistically significant change, in the formation of the complex in the sample or subject relative to the control sample or subject can be indicative of the presence of α-enolase I in the sample.

Complex formation between the α-enolase I antibody and α-enolase I can be detected by measuring or visualizing either the ligand bound to the α-enolase I or unbound ligand. Conventional detection assays can be used, e.g., an enzyme-linked immunosorbent assays (ELISA), a radioimmunoassay (RIA) or tissue immunohistochemistry. Further to labeling the α-enolase I antibody, the presence of α-enolase I can be assayed in a sample by a competition immunoassay utilizing standards labeled with a detectable substance and an unlabeled α-enolase I antibody.

Kits

An anti-α-enolase I antibody or fragment thereof, can be provided in a kit, e.g., as a component of a kit. For example, the kit includes (a) an anti-α-enolase I antibody or fragment thereof, e.g., a composition that includes an anti-α-enolase I antibody or fragment thereof, and, optionally (b) informational material. The informational material can be descriptive, instructional, marketing, or other material that relates to the methods described herein and/or the use of an anti-α-enolase I antibody or fragment thereof, for the methods described herein.

The informational material of the kits is not limited in its form. In one embodiment, the informational material can include information about production of the compound, molecular weight of the compound, concentration, date of expiration, batch, or production site information, and so forth. In one embodiment, the informational material relates to using the ligand to treat, prevent or diagnose a disorder described herein.

The kit can include one or more containers for the composition containing an anti-α-enolase I antibody or fragment thereof. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial, or syringe that has attached thereto the informational material in the form of a label. In some embodiments, the kit includes a plurality (e.g., a pack) of individual containers, each containing one or more unit dosage forms (e.g., a dosage form described herein) of an anti-α-enolase I antibody or fragment thereof. For example, the kit includes a plurality of syringes, ampules, foil packets, atomizers, or inhalation devices, each containing a single unit dose of an anti-α-enolase I antibody or fragment thereof, or multiple unit doses.

The kit optionally includes a device suitable for administration of the composition, e.g., a syringe, pipette, forceps, measured spoon, dropper (e.g., eye dropper), swab (e.g., a cotton swab or wooden swab), or any such delivery device. In a preferred embodiment, the device is an implantable device that dispenses metered doses of the ligand.

The Examples which follow are set forth to aid in the understanding of the inventions but are not intended to, and should not be construed to, limit its scope in any way.

EXAMPLE

Example 1

Characterization of Purified Recombinant α-Enolase and Polyclonal Anti-α-Enolase IgY Antibodies The gene encoding α-enolase protein was cloned out from PE089 cells by reverse transcription-PCR using gene-specific primers 5'-GGTGGAATTCTATCTATTCTCAAGATC-CATGCC-3' (SEQ ID NO: 41) (forward) and 5'-ACTC-CATGGTTACTTGGCCAAGGGGTTTCT-3' (SEQ ID NO: 42) (reverse). The resultant PCR fragment was cloned into pGEX-KG vector at EcoRI and NcoI sites and transformed into the *E. coli* BL-21 (DE3) strain for its expression. The gene was also subcloned into pET2la vector using 5'-CCGCGTGAATTCGGGGATCCATGTCTAT-TCTCAAGATCC-3' (SEQ ID NO: 43) (forward) and 5'-CATGGAGTCGACCTCGAGCTTGGC-CAAGGGGTTTCTG-3' (SEQ ID NO: 44) (reverse) and expressed as His-fused α-enolase. Individual clone was grown in 5 ml LB medium containing ampicillin (100 μg/ml) at 37° C. overnight. The bacterial culture was diluted 10-fold in the same LB medium and further grown until the $OC_{600}$ reached between 0.6 and 1.0. To induce GST-fused or His-fused α-enolase protein expression, iso-propyl-β-D-thioga-lactopyranoside (IPTG) was added to a final concentration of 0.5 mM in the culture. The cell pellet was resuspended in 2 ml of 1× PBS containing 1% Triton x-100 and lysed by three cycles of freezing (−70° C.) and thawing (37° C.). After centrifugation, the resulting cellular lysate was incubated with Glutathione Sepharose 4B or $Ni^{2+}$-charged resin column to purify the α-enolase protein according to the manufacturer's instruction (General Electronics, Piscataway, N.J., USA).

After electrophoresis and Coomassie blue staining, purified His-fused and GST-fused α-enolase were visualized as a single band of 48 kD and 75 kD (lanes 2 and 3 in FIG. 1A, respectively). The identity of GST-fused α-enolase was verified using anti-GST antibodies as shown in lane 3, FIG. 1B. Similarly, polyclonal IgY antibodies produced in chickens immunized with purified His-fused α-enolase were able to clearly recognize both His-fused and GST-fused α-enolase immobilized on Western blots (lanes 2 and 3 in FIG. 1C).

Example 2

Chicken Immunization

Female white leghorn (*Gallus domesticus*) chickens were immunized with 100 purified α-enolase in an equal volume of Freund's complete adjuvant by an intramuscular injection. Three additional immunizations with incomplete adjuvant were performed at intervals of 7 days. After each immunization, IgY antibodies in sera and egg yolk were collected and titrated by an enzyme-linked immunosorbent assay (ELISA) to determine the presence of humoral anti-α-enolase immune response. Egg yolk was separated from the egg white for IgY purification using 10% Dextran sulphate as described previously (Akita and Nakai, 1993a, b). The purified total IgY antibodies from each egg was dissolved in 5 ml of TBS containing 0.05% sodium azide and stored at −20° C.

Figure 2:
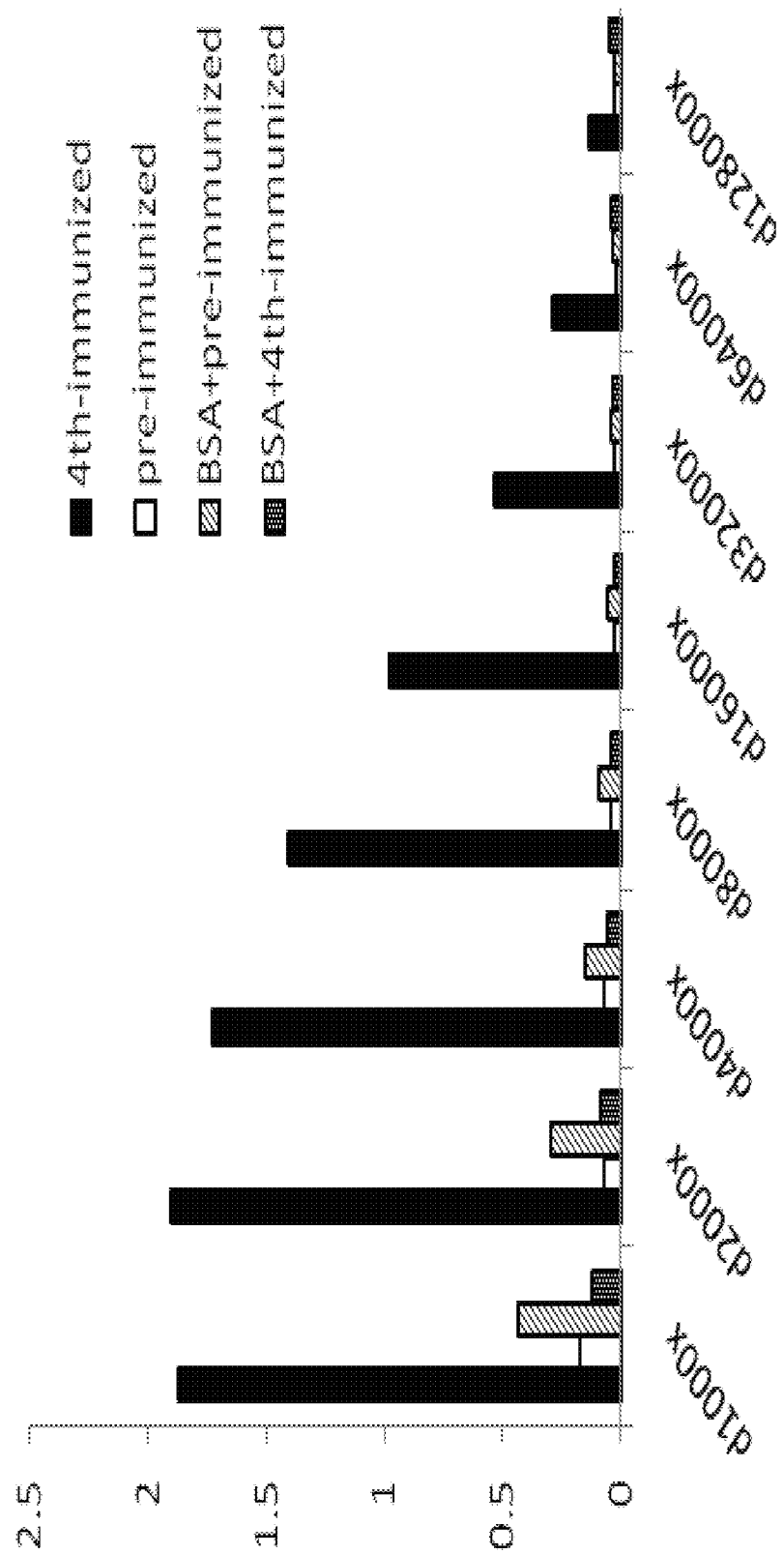
FIG. 2 is humoral IgY responses in chicken after 4th immunization analyzed by ELISA. Purified α-enolase protein and bovine serum antigen (BSA) were coated on plate wells. A series of diluted IgY antibodies were examined for their specific binding activity to either α-enolase or BSA. Solid and open bars represent the binding of IgY from 4th- or pre-immunized chickens to α-enolase, respectively. In addition, their binding to BSA presented by deep and light gray bars were shown in parallel as negative controls.

Sera and eggs were collected from chickens before and after each immunization. Total IgY antibodies in egg yolk were purified and detected the presence of both heavy and light chain fragments using anti-chicken IgY antibodies conjugated horse radish peroxidase (data not shown). The purified IgY was used to test for their binding activity to α-enolase immobilized on nitrocellulose membrane (FIG. 1C) or ELISA plate wells. As shown in FIG. 2, the IgY antibodies prepared from the egg yolk after 4th immunization specifically bind to α-enolase but not bovine serum albumin when titered at 1:16,000 dilution, suggesting a strong humoral antibody response was elicited in the chicken host. In contrast, the IgY antibodies from pre-immunized chicken eggs showed very little binding signal to both antigens.

Example 3

Construction of scFv Antibody Library and Biopanning

The antibody library was established based on the previous report: Andris-Widhopf, J., Rader, C., Steinberger, P., Fuller, R., Barbas, C. F., 3rd, 2000, Methods for the generation of chicken monoclonal antibody fragments by phage display. J Immunol Methods 242, 159-181) . Briefly, chicken spleens were harvested and placed immediately in Trizol reagent for homogenization 7 days following the final immunization. Ten μg of total RNAs was reversely transcribed into the first-strand cDNA using a SuperScript RT kit (Invitrogen, USA). After amplified using chicken-specific primers, PCR products of heavy and light chain variable (VH and VL) regions were subjected to a second round of PCR with a short or long linker to form full-length scFv fragments, which were further digested with SfiI and cloned into the pComb3X vector. Recombinant DNAs were transformed into $E.\ coli$ XL-1 blue strain by electroporation. Recombinant phage production was initiated by the addition of VCS-M13 helper phage, precipitated with 4% polyethylglycol 8000 and 3% NaCl (w/v), and finally re-suspended in phosphate-buffered saline (PBS) containing 1% bovine serum albumin (BSA) and stored at 4° C. Then, $10^{11}$ plaque-forming units (pfu) of recombinant phages from scFv antibody library were added to wells pre-coated with α-enolase protein (0.5 μg/well), and incubated at 37° C. for 2 h. After removing unbound phages, bound phages were eluted with 0.1 M HCl/glycine (pH 2.2)/ 0.1% BSA, neutralized with 2 M Tris base buffer and used to infect the XL-1 blue strain. The amplified phages were precipitated and recovered as described above for the next round of selection. The panning procedure was repeated three or four times. A panel of clones were randomly selected and grown from the final panning process. After 0.5 mM IPTG induction for 6 hrs, bacterial cells were collected and lysed by three cycles of freezing and thawing and/or sonication. The supernatants were analyzed for their scFv antibody expression and binding reactivity to α-enolase using Western blotting and ELISA. ScFv antibodies expressed in TOP 10F' $E.\ coli$ (Invitrogen, a nonsuppressor strain) and purified using $Ni^{2+}$-charged sepharose as described by the manufacturer (Amersham Biosciences, UK) were also prepared in flow cytometric and immunofluoresence analyses.

Figure 3:
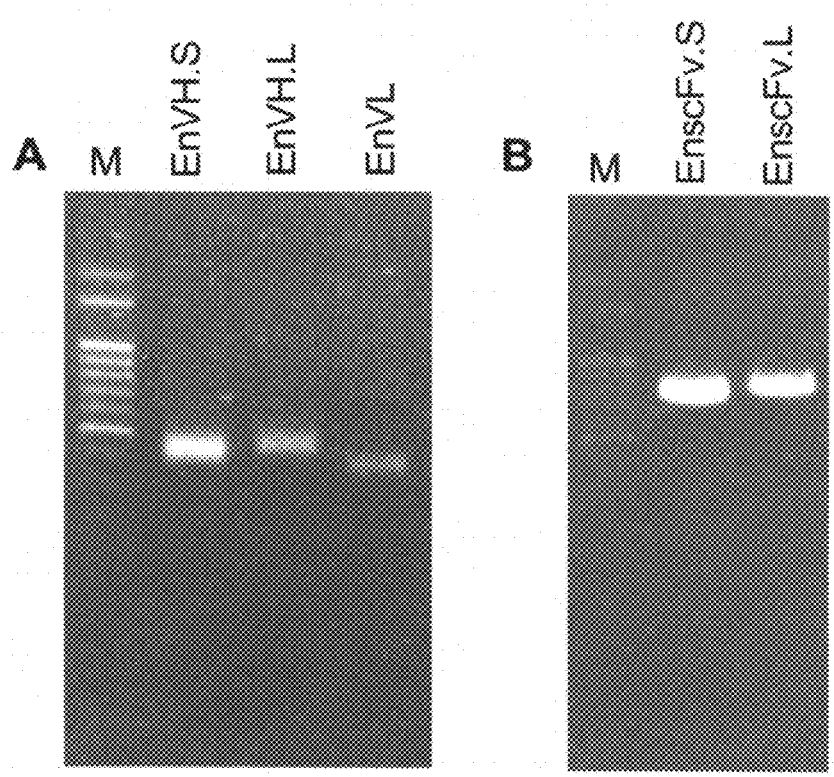
FIG. 3 is PCR amplification of the variable regions in chicken immunoglobulin genes. Variable regions of the light chain (EnVL) and heavy chain with short linker (EnVH.S) or with long linker (EnVH.L) were amplified successfully (panel A). The second round of PCR generated the full-length scFv gene fragments with short (EnscFv.S) or long (EnscFv.L) linkers (panel B).

The chickens were sacrificed eight weeks after the last immunization and the total RNAs were extracted from the enlarged spleens for antibody library construction. The amplification of full-length scFv gene fragments was carried out using 2 consecutive PCR steps. In the primary PCR, VH gene products were amplified as 400 bp in size using primers containing short (GGSSRSS) (SEQ ID NO: 45) and long (GGSSRSSSSGGGGSGGGG) (SEQ ID NO: 46) linkers as presented as EnVH.S (FIG. 3A, lane 2) and EnVH.L (FIG. 3A, lane 3), respectively. Accordingly, the VL gene was amplified as a band of 350 bp and loaded in lane 4 in FIG. 3A (EnVL). Subsequently, the amplified VH and VL were joined to form full-length scFv gene fragments of approximately 750 bp presented as EnscFv.S (lane 2) and EnscFv.L (lane 3) in FIG. 3B. Several phage displaying antibody libraries were constructed and used to screen the specific anti-α-enolase scFv antibodies.

Example 4

Characterization of Anti-α-Enolase scFv Clones

To detect the scFv antibody expression, the cellular lysates were subjected to sodium dodecyl sulfate polyacrylamide gel electrophoresis (SDS-PAGE). All the proteins were transferred onto nitrocellulose membranes (Amersham Biosciences, UK), which were then blocked with 5% skim milk in TBST for 1 hr. Polyclonal goat anti-chicken IgY light chain antibodies (Bethyl Laboratories, Montgomery, Tex., USA) were added at 1:3000 dilution and incubated for an additional hr. The membranes were washed with TBST three times for 5 min each. The bound antibodies were detected by adding horseradish peroxidase (HRP)-conjugated donkey anti-goat Ig antibodies (Sigma, St. Louis, Mo., USA) at 1:3000 dilution. After three washings, the membranes were developed with diaminobenzidine (DAB) substrate until the desired intensity was reached. To examine their binding reactivity, the IgY purified from 4th immunized chicken or the expressed scFv antibodies were incubated with the purified α-enolase immobilized on nitrocellulose membranes or ELISA plate wells and subsequently detected by adding goat anti-chicken IgY light chain and HRP-conjugated donkey anti-goat Ig antibodies as described above. The ELISA tests were done in the duplicated wells for each sample.

Figure 4:
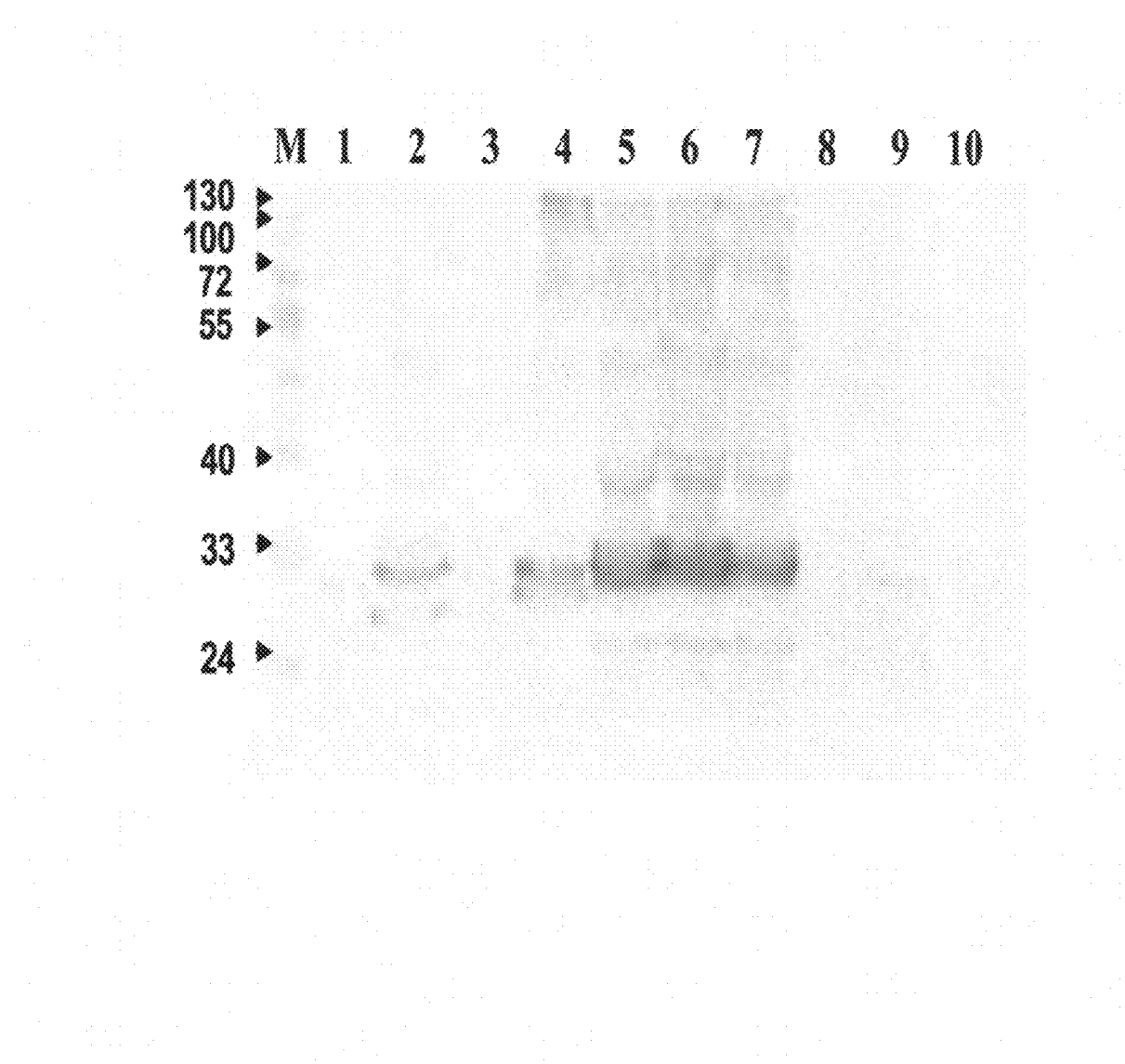
FIG. 4 is expression of scFv antibodies analyzed by Western blotting. Identical amount of total cellular lysates from 30 clones were loaded onto SDS-PAGE and transferred to nitrocellulose papers. The presence of scFv antibodies was detected by goat anti-chicken light chain antibodies at 1:3000 dilution, followed by HRP-conjugated donkey anti-goat IgG. The predicted molecular weight of scFv fragment is approximately 35 kDa. The blot is a representative result of scFv expression in 10 selected clones.

Four rounds of panning cycles were carried out as described above. After each panning, fifteen clones were randomly selected and analyzed for 750 bp fragment inserts in pCom3X cloning vector and their scFv antibody protein expression. Our data (not shown) indicated that 67% (10/15), 87% (13/15), 100% (15/15) and 100% (15/15) of clones from each round of panning had the full-length inserts. Moreover, ten clones with 750 bp inserts from the last round of panning were induced to express their scFv antibodies. As seen in FIG. 4, we clearly detected the scFv expression in clones EnL2, EnL4, EnL5, EnL6 and EnL7 whereas little or no expression was detected in clones EnL1, EnL3, EnL8, EnL9 and EnL10 using goat anti-chicken IgY light chain antibodies and horseradish peroxidase (HRP)-conjugated donkey anti-goat Ig antibodies. These results indicated that the expression level of immunoglobulin genes with highly conserved sequences could be dramatically different even under the identical experimental conditions.

Example 5

Gene Sequencing and ELISA Analysis

The nucleotide sequence determination of heavy and light variable regions from chosen clones was carried out by an auto-sequencer machine (ABI PRISM 377; Perkin-Elmer, National Health Research Institute) using ompseq (5'-AAGACAGCTATCGCGATTGCAGTG-3') (SEQ ID NO: 47) and HRML-F (5'-GGTGGTTCCTCTAGATCTTCC-3') (SEQ ID NO: 48) primers. The results were analyzed using alignment program BLAST and Vector NTI (http://www.ncbi.nlm.nih.gov/BLAST).

Figure 5:
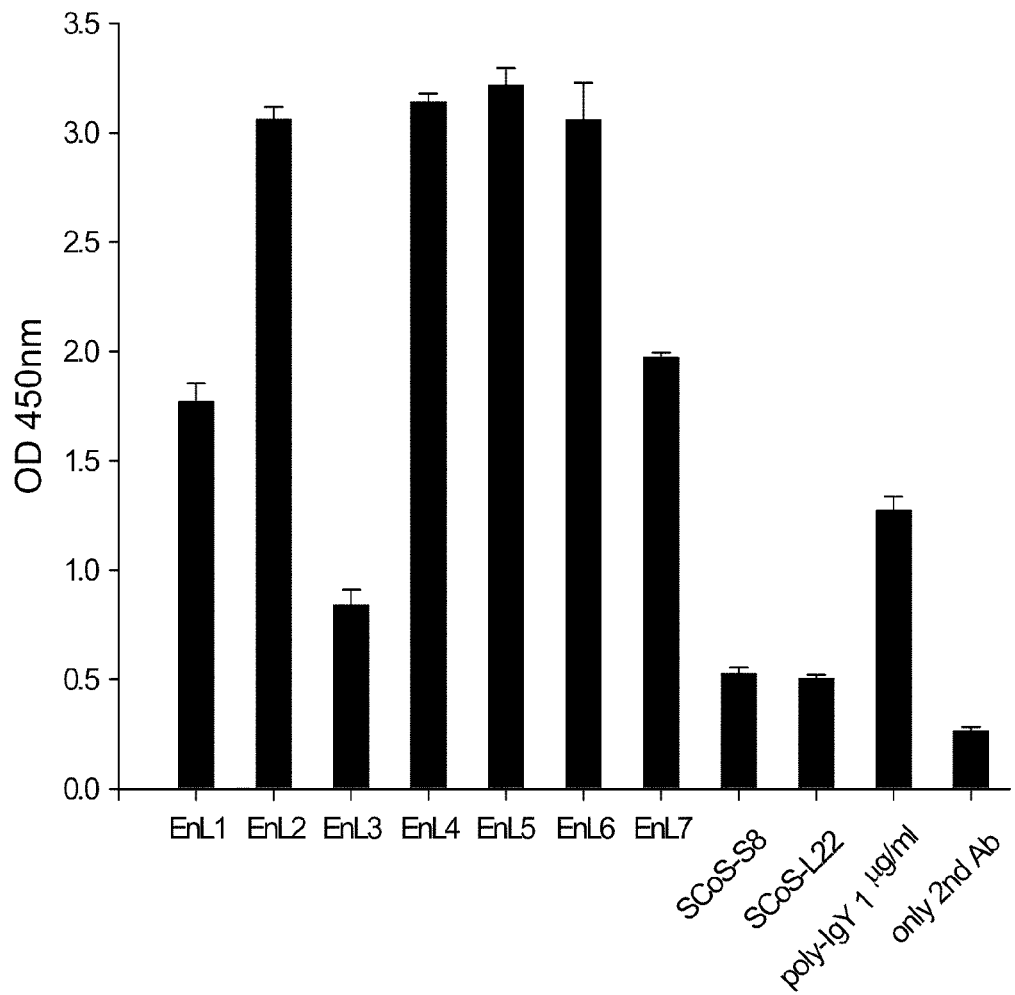
FIG. 5 is binding activity of scFv antibodies to purified α-enolase analyzed by ELISA. Cellular lysates containing scFv antibodies from randomly selected clones from the 4th panning cycle were examined for their binding to purified α-enolase coated onto the plate wells. Binding activity was detected using the goat anti-chicken light chain antibodies at 1:3000 dilution, followed by HRP-conjugated donkey anti-goat IgG and measured at 450 nm. Two anti-SARS-CoV scFv antibodies (SCoS-S8 and SCoS-L22) were used as negative controls. One additional control experiment was carried out as described without adding primary recombinant scFv antibodies. Polyclonal IgY antibodies from chickens immunized with purified α-enolase were used as a positive control. The ELISA data were represented as means of the duplicated experiments.
Figure 6:
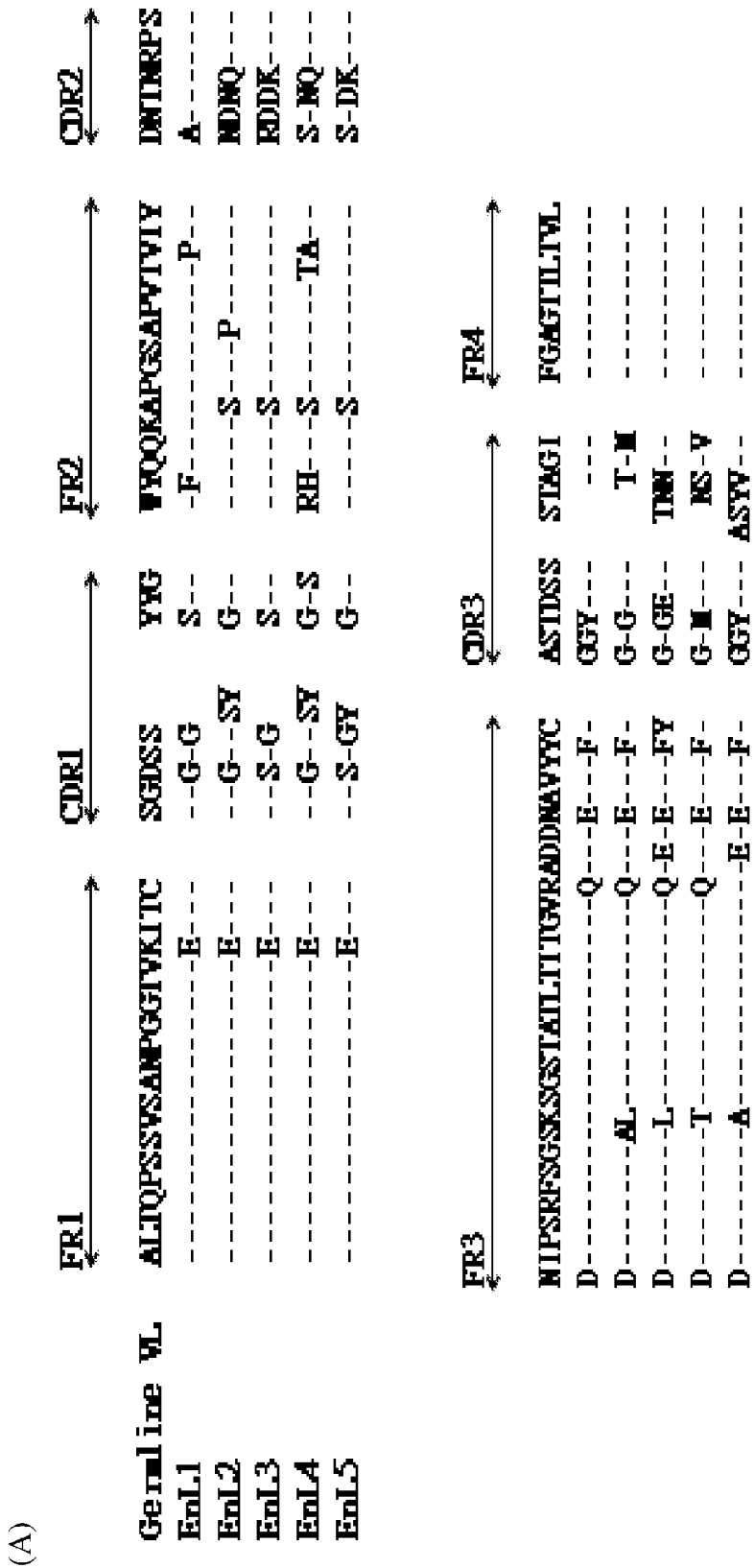
FIG. 6 is sequence analysis of $V_L$ (FIG. 6(A)) and $V_H$ (FIG. 6(B)) sequences of scFv antibodies. The nucleotide sequences of $V_H$ and $V_L$ of 10 clones were determined and translated into amino acid sequences to be aligned with those of the chicken germline gene. FR: framework region; CDR: complementarity determining region. Sequence gaps were introduced to maximize the alignment and indicated by blank spaces. Dots indicated the consensus sequences. Framework region (FR) and complementarity-determining region (CDR) boundaries were indicated above germline sequences.
Figure 6:
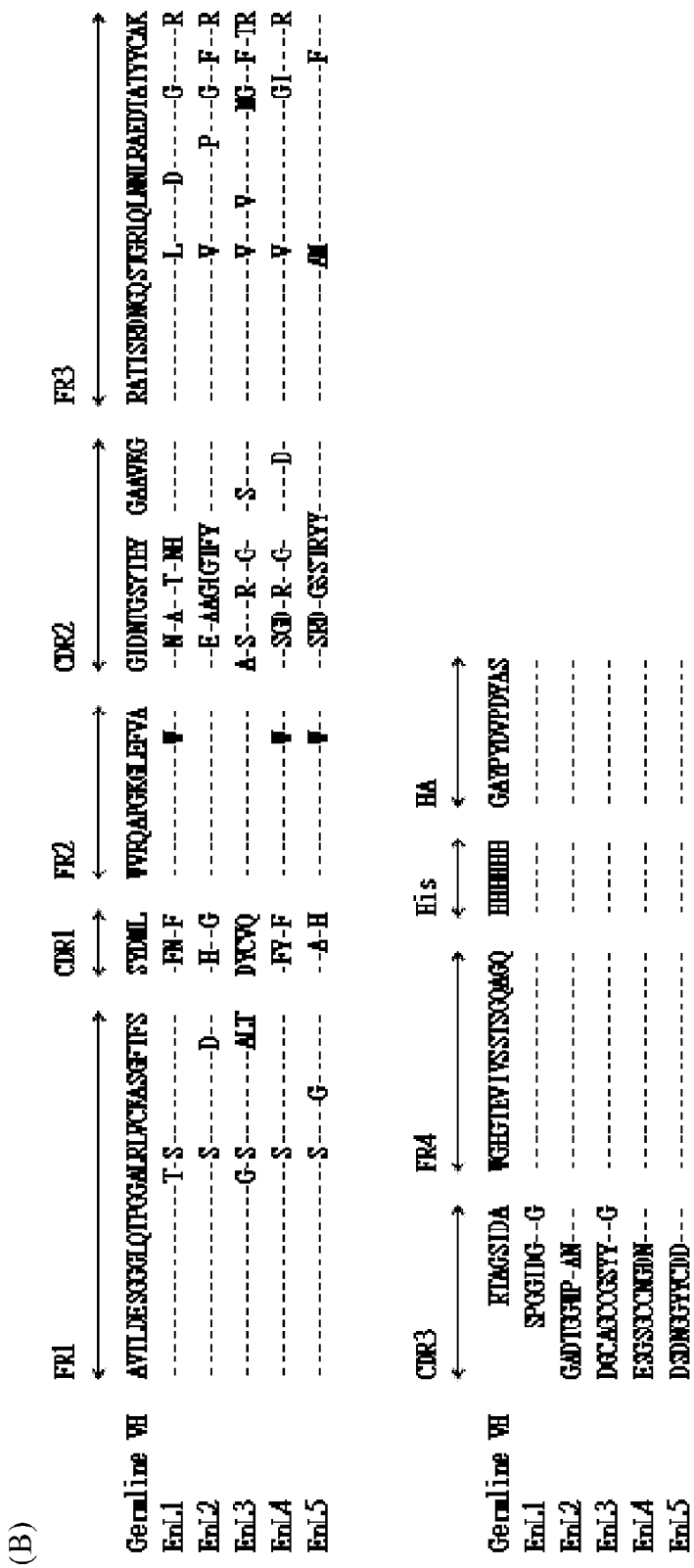

The nucleotide sequences of the variable regions of heavy and light chain genes of 10 clones were determined and aligned to the germline gene sequences of chicken immunoglobulin. The results revealed that 30% of the sequenced clones (EnL5, EnL6 and EnL7) shared identical heavy and light genes leading to the similar profiles of their scFv antibody expression as seen in lanes 5, 6 and 7 in FIG. 4. The overall mutation rates as compared to the germline gene sequences range from 18.6 to 27.4% and from 13.5 to 23.1% in heavy and light chain variable regions respectively (FIG. 5). The binding activities of the expressed EnL1 to EnL7 scFv antibodies against α-enolase were analyzed using ELISA. It is found that those scFv antibody fragments exhibit significant binding activity to α-enolase as compared to 2 other scFv antibodies which were previously characterized and known to specifically recognize SARS-CoV spike protein. In particular, EnL2, EnL4, EnL5 and EnL6 scFv antibodies showed stronger positive reactivity than polyclonal IgY purified from chicken immunized with human α-enolase molecule (FIGS. 6(A) and (B)).

Example 6

Flowcytometry Analysis

The PE089 cell line was originally obtained from effusion tumor cells of a 36-year-old patient with stage IV lung adenocarcinoma, which was kindly provided by Dr. Neng-Yao Shih from National Institute of Cancer Research, National Health Research Institutes, Tainan, Taiwan. The cells have been cultured in RPMI 1640 supplemented with 5% fetal bovine serum, 2 mmol/L glutamine, and antibiotics for at least 40 passages in vitro. A total of $2 \times 10^6$ cells was harvested and fixed with 2% paraformaldehyde as described previously. The α-enolase expressed in the PE089 cells was detected with purified scFv EnL2 and EnL5 antibodies, visualized with mouse anti-HA (1:200) and goat anti-mouse antibodies conjugated with Cy-2 (1:200) (Jackson ImmunoResearch Laboratories, West Grove, Pa., USA), and analyzed using the FACScan flow cytometer (Becton Dickinson, Franklin Lakes, N.J., USA). Negative controls were performed as described above with omitting the primary scFv EnL2 and EnL5 antibodies while positive controls were performed using rabbit polyclonal anti-human enolase antibodies (1:200) instead of scFv EnL2 and EnL5 antibodies.

Figure 7:
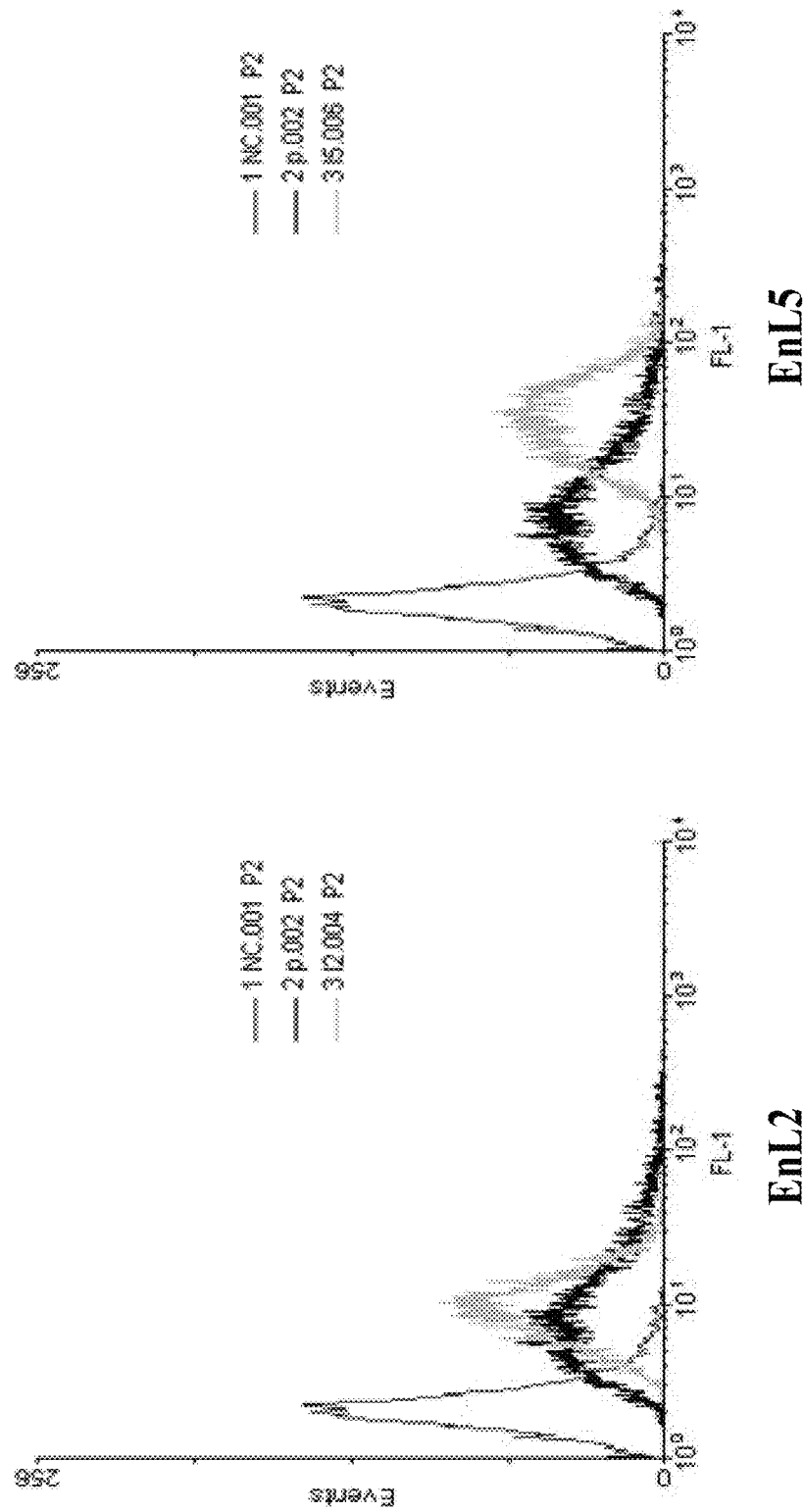
FIG. 7 is binding activity of scFv antibodies to purified α-enolase analyzed by
Flowcytometry. Surface associated α-enolase on PE089 cells was detected using purified EnL2 and EnL5 scFv antibodies, mouse anti-HA (1:200) and Cy-2-conjugated goat anti-mouse antibodies (1:200). The grey thin lines indicate negative control, cells treated with DMSO alone and stained with fluorescence-labeled Abs against surface markers; the gray solid lines indicate cells stained with fluorescence-labeled Ig isotype controls; and the black solid lines indicate cells stained with scFv antibodies EnL2 and EnL5 fluorescence-labeled Abs against surface α-enolase. The results of one representative experiment of three separate experiments are shown.

To test the binding reactivity of these cloned scFv antibodies, human α-enolase gene was transfected into PE089 tumor cells for its expression on the membrane surface which was subsequently analyzed by flow cytometry. EnL2 and EnL5 scFv antibodies purified as a single band on SDS-PAGE (data not shown) were able to detect recombinant α-enolase protein expressed in PE089 cells, which binding signal is comparable to that of commercially available rabbit polyclonal antibodies specific for α-enolase as demonstrated in FIG. 7.

Example 7

Immunofluorescence and Laser Scanning Microscopy

PE089 cells ($2 \times 10^5$ cells/ml) were seeded on cover glass and fixed by incubating with equal volume of ice cold 8% paraformaldehyde (freshly prepared) on ice for 15 min. After fixing, the cells were dehydrated in a sequential treatment of 70%, 95% and 99% methanol and rehydrated with 95% and 70% methanol. The slides were then over-laid with blocking buffer (1% BSA in 1× PBS) at RT for 1 hr. Following washing with 1× PBS, scFv antibodies were incubated with cells at RT for one additional hr. Finally, their binding to α-enolase protein was detected by mouse anti-HA antibodies, followed by goat anti-mouse antibodies conjugated with Cy-2. Nuclei were also counterstained with PI solution as suggested (Invitrogen, USA). The slides were subjected to a Confocal Spectral Microscope Imaging System (TCS SP5, Leica) for observation.

Figure 8:
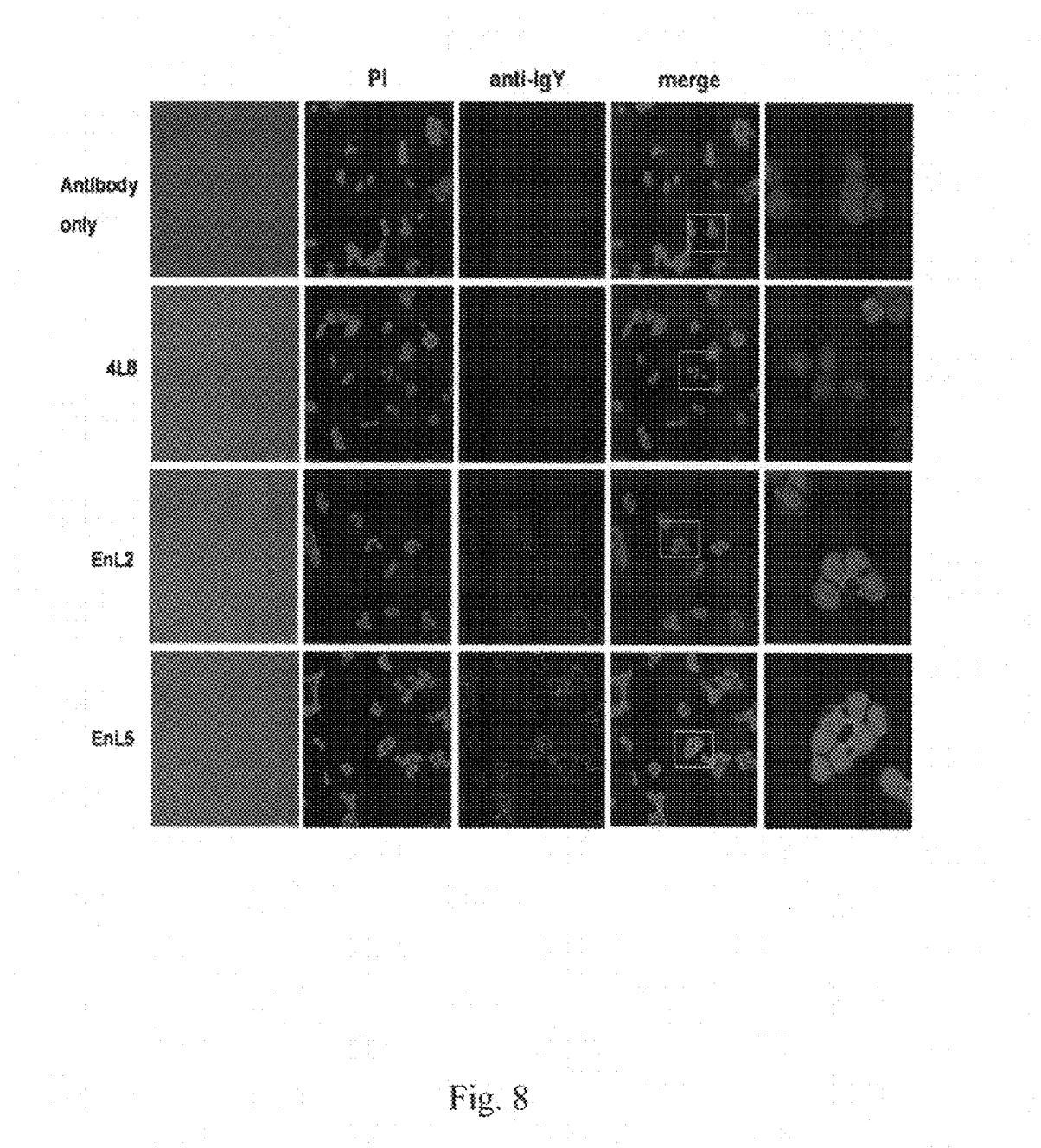
FIG. 8 is immunofluorescent staining of α-enolase protein in PE089 cells. Cells were fixed on the glass plates as described in "Materials and Methods". The α-enolase expression was detected using purified EnL2 and EnL5 scFv antibodies, followed by mouse anti-HA and Cy-2-conjugated goat anti-mouse antibodies. The nucleus (red) was visualized by PI. Both EnL2 and EnL5 scFv antibodies clearly stained nuclear membrane (green) in PE089 cells. An anti-SARS-CoV scFv antibody, 4L8, did not show any reactivity with nuclear membrane.

We also applied immunocytochemical staining to assess the binding ability of purified EnL2 and EnL5 scFv antibodies against α-enolase molecule expressed in PE089 cells. It has been demonstrated that the α-enolase molecule is mainly expressed and translocated on the nucleic membrane of PE089 cells (personal communication with Dr. N-Y Shih). Accordingly, our recombinant EnL2 and EnL5 scFv antibodies exhibited significant binding signal around the cell nuclei membrane as shown in FIG. 8. In contrast, two negative controls including goat anti-mouse antibodies conjugated with Cy-2 or 4L8 clone expressing a scFv antibody specific for SARS-CoV spike protein showed no reactivity at all. The cell morphology and distribution under light microscopy are included in the most left panel for comparison. Taken together, the results provided further evidence to show that phage display technology might be an better alternative for the cloning and generation of scFv antibodies against specific antigens.

What is claimed is:

1. A purified monoclonal antibody, or antigen-binding fragment thereof, comprising a heavy chain immunoglobulin variable domain and a light chain immunoglobulin variable domain that binds to α-enolase I, wherein the light chain immunoglobulin variable domain comprises the amino acid sequence of: (i) SGGSGSYG (SEQ ID NO: 1), SGGSSSYGYG (SEQ ID NO: 2), SGSSGSYG (SEQ ID NO: 3), SGGSSSYGYS (SEQ ID NO: 4) or SGSSGYGYG (SEQ ID NO: 5) in CDR1, (ii) ANTNRPS (SEQ ID NO: 6), NDNQRPS (SEQ ID NO: 7), RDDKRPS (SEQ ID NO: 8), SNNQRPS (SEQ ID NO: 9) or SNDKRPS (SEQ ID NO: 10) in CDR2, and (iii) GGYDSSAGI (SEQ ID NO: 11), GSGDSSTGM (SEQ ID NO: 12), GSGESSTNNGI (SEQ ID NO: 13), GSMDSSNSGV (SEQ ID NO: 14) or GGYDSSASYVGI (SEQ ID NO: 15) in CDR3; and wherein the heavy chain immunoglobulin variable domain comprises the amino acid sequence of: (i) SFNMF (SEQ ID NO: 16), SHDMG (SEQ ID NO: 17), DYCVQ (SEQ ID NO: 18), SFYMF (SEQ ID NO: 19) or SYAMH (SEQ ID NO: 20) in CDR1, (ii) GINNAGSTTNHGAAVKG (SEQ ID NO: 21), GIENAAGIGTFYGAAVKG (SEQ ID NO: 22), AISNTGRYTGYGSAVKG (SEQ ID NO: 23), GISGDGRYTGYGAAVDG (SEQ ID NO: 24) or GISRDGGSSTRYYGAAVKG (SEQ ID NO: 25) in CDR2, and (iii) SPGGIDGIDG (SEQ ID NO: 26), GADTGGWPAANIDA (SEQ ID NO: 27), DGCAGCCGSYYIDG (SEQ ID NO: 28) ESGSGCCNGDNIDA (SEQ ID NO: 29) or DSDNGGYYCDDIDA (SEQ ID NO: 30) in CDR3.

2. The purified monoclonal antibody, or antigen-binding fragment thereof, of claim 1, which comprises framework regions from VH and VL FR1, FR2, FR3 and FR4 framework regions encoded by germline gene sequence of chicken immunoglobulin (SEQ ID NO:31) or an amino acid sequence at least 85% identical to the VH and VL FR1, FR2 and FR3 framework regions encoded by the germline gene sequence of chicken immunoglobulin (SEQ ID NO:31).

3. The purified monoclonal antibody, or antigen-binding fragment thereof, of claim 2, which comprises framework regions from an amino acid sequence at least 87%, 88%, 89%, 90%, 91%, 92%, 93%, 94%, 95%, 97%, 98%, or 99% identical to the VH and VL FR1, FR2 and FR3 framework regions encoded by the germline gene sequence of chicken immunoglobulin (SEQ ID NO:31).

4. The purified monoclonal antibody, or antigen-binding fragment thereof, of claim 1, which comprises VL complementarity determining region having an amino acid sequence selected from the group consisting of the following amino acid sequences: i) SEQ ID NO:1 in CDR1, SEQ ID NO: 6 in CDR2 and SEQ ID NO: 11 in CDR3; ii) SEQ ID NO:2 in CDR1, SEQ ID NO: 7 in CDR 2 and SEQ ID NO: 12 in CDR3; iii) SEQ ID NO: 3 in CDR1, SEQ ID NO: 8 in CDR 2 and SEQ ID NO: 13 in CDR3; iv) SEQ ID NO: 4 in CDR 1, SEQ ID NO: 9 in CDR 2 and SEQ ID NO: 14 in CDR3 and v) SEQ ID NO: 5 in CDR1, SEQ ID NO: 10 in CDR2 and SEQ ID NO: 15 in CDR3.

5. The purified monoclonal antibody, or antigen-binding fragment thereof, of claim 1, which comprises VL complementarity determining region having an amino acid sequence selected from the group consisting of the following amino acid sequences: ii) SEQ ID NO:2 in CDR1, SEQ ID NO: 7 in CDR 2 and SEQ ID NO: 12 in CDR3; and v) SEQ ID NO: 5 in CDR1, SEQ ID NO: 10 in CDR2 and SEQ ID NO: 15 in CDR3.

6. The purified monoclonal antibody, or antigen-binding fragment thereof, of claim 1, comprises VL complementarity determining region having an amino acid sequence selected from the group consisting of SEQ ID NOs: 31-35 and VH complementarity determining region having an amino acid sequence selected from the group consisting of SEQ ID NOs: 36-40.

7. The purified monoclonal antibody, or antigen-binding fragment thereof, of claim 6, comprises VL complementarity determining region having an amino acid sequence of SEQ ID NO: 32 or SEQ ID NO: 35 and VH complementarity determining region having an amino acid sequence of SEQ ID NO: 37 or SEQ ID NO: 40.

8. A pharmaceutical composition, comprising the monoclonal antibody of claim 1 and a pharmaceutically acceptable carrier.

9. A kit for the detection of the presence of an α-enolase I in a sample, comprising an anti-α-enolase I antibody of claim 1 or fragment thereof, and optionally an informational material.

10. The kit of claim 9, wherein the anti-α-enolase I antibody is the monoclonal antibody of claim 6.

* * * * *

SEQUENCE LISTING

```
<160> NUMBER OF SEQ ID NOS: 50

<210> SEQ ID NO 1
<211> LENGTH: 8
<212> TYPE: PRT
<213> ORGANISM: Artificial Sequence
<220> FEATURE:
<223> OTHER INFORMATION: Synthetic sequence

<400> SEQUENCE: 1

Ser Gly Gly Ser Gly Ser Tyr Gly
1               5

<210> SEQ ID NO 2
<211> LENGTH: 10
<212> TYPE: PRT
<213> ORGANISM: Artificial Sequence
<220> FEATURE:
```

```
<223> OTHER INFORMATION: CDR1 of VL of EnL2

<400> SEQUENCE: 2

Ser Gly Gly Ser Ser Ser Tyr Gly Tyr Gly
1               5                   10

<210> SEQ ID NO 3
<211> LENGTH: 8
<212> TYPE: PRT
<213> ORGANISM: Artificial Sequence
<220> FEATURE:
<223> OTHER INFORMATION: CDR1 of VL of ENL3

<400> SEQUENCE: 3

Ser Gly Ser Ser Gly Ser Tyr Gly
1               5

<210> SEQ ID NO 4
<211> LENGTH: 10
<212> TYPE: PRT
<213> ORGANISM: Artificial Sequence
<220> FEATURE:
<223> OTHER INFORMATION: CDR1 of VL of ENL4

<400> SEQUENCE: 4

Ser Gly Gly Ser Ser Ser Tyr Gly Tyr Ser
1               5                   10

<210> SEQ ID NO 5
<211> LENGTH: 9
<212> TYPE: PRT
<213> ORGANISM: Artificial Sequence
<220> FEATURE:
<223> OTHER INFORMATION: CDR1 of VL of EnL5

<400> SEQUENCE: 5

Ser Gly Ser Ser Gly Tyr Gly Tyr Gly
1               5

<210> SEQ ID NO 6
<211> LENGTH: 7
<212> TYPE: PRT
<213> ORGANISM: Artificial Sequence
<220> FEATURE:
<223> OTHER INFORMATION: CDR2 of VL of EnL1

<400> SEQUENCE: 6

Ala Asn Thr Asn Arg Pro Ser
1               5

<210> SEQ ID NO 7
<211> LENGTH: 7
<212> TYPE: PRT
<213> ORGANISM: Artificial Sequence
<220> FEATURE:
<223> OTHER INFORMATION: CDR2 of VL of EnL3

<400> SEQUENCE: 7

Asn Asp Asn Gln Arg Pro Ser
1               5

<210> SEQ ID NO 8
<211> LENGTH: 7
<212> TYPE: PRT
<213> ORGANISM: Artificial Sequence
<220> FEATURE:
<223> OTHER INFORMATION: CDR2 of VL of EnL3
```

```
<400> SEQUENCE: 8

Arg Asp Asp Lys Arg Pro Ser
1               5

<210> SEQ ID NO 9
<211> LENGTH: 7
<212> TYPE: PRT
<213> ORGANISM: Artificial Sequence
<220> FEATURE:
<223> OTHER INFORMATION: CDR2 of VL of EnL4

<400> SEQUENCE: 9

Ser Asn Asn Gln Arg Pro Ser
1               5

<210> SEQ ID NO 10
<211> LENGTH: 7
<212> TYPE: PRT
<213> ORGANISM: Artificial Sequence
<220> FEATURE:
<223> OTHER INFORMATION: CDR2 of VL of EnL5

<400> SEQUENCE: 10

Ser Asn Asp Lys Arg Pro Ser
1               5

<210> SEQ ID NO 11
<211> LENGTH: 9
<212> TYPE: PRT
<213> ORGANISM: Artificial Sequence
<220> FEATURE:
<223> OTHER INFORMATION: CDR3 of VL of EnL1

<400> SEQUENCE: 11

Gly Gly Tyr Asp Ser Ser Ala Gly Ile
1               5

<210> SEQ ID NO 12
<211> LENGTH: 9
<212> TYPE: PRT
<213> ORGANISM: Artificial Sequence
<220> FEATURE:
<223> OTHER INFORMATION: CDR3 of VL of EnL2

<400> SEQUENCE: 12

Gly Ser Gly Asp Ser Ser Thr Gly Met
1               5

<210> SEQ ID NO 13
<211> LENGTH: 11
<212> TYPE: PRT
<213> ORGANISM: Artificial Sequence
<220> FEATURE:
<223> OTHER INFORMATION: CDR3 of VL of EnL3

<400> SEQUENCE: 13

Gly Ser Gly Glu Ser Ser Thr Asn Asn Gly Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: CDR3 of VL of EnL4

<400> SEQUENCE: 14
```

```
Gly Ser Met Asp Ser Ser Asn Ser Gly Val
1               5                   10

<210> SEQ ID NO 15
<211> LENGTH: 12
<212> TYPE: PRT
<213> ORGANISM: Artificial Sequence
<220> FEATURE:
<223> OTHER INFORMATION: CDR3 of VL of EnL5

<400> SEQUENCE: 15

Gly Gly Tyr Asp Ser Ser Ala Ser Tyr Val Gly Ile
1               5                   10

<210> SEQ ID NO 16
<211> LENGTH: 5
<212> TYPE: PRT
<213> ORGANISM: Artificial Sequence
<220> FEATURE:
<223> OTHER INFORMATION: CDR1 of VH of EnL1

<400> SEQUENCE: 16

Ser Phe Asn Met Phe
1               5

<210> SEQ ID NO 17
<211> LENGTH: 5
<212> TYPE: PRT
<213> ORGANISM: Artificial Sequence
<220> FEATURE:
<223> OTHER INFORMATION: CDR1 of VH of EnL2

<400> SEQUENCE: 17

Ser His Asp Met Gly
1               5

<210> SEQ ID NO 18
<211> LENGTH: 5
<212> TYPE: PRT
<213> ORGANISM: Artificial Sequence
<220> FEATURE:
<223> OTHER INFORMATION: CDR1 of VH of EnL3

<400> SEQUENCE: 18

Asp Tyr Cys Val Gln
1               5

<210> SEQ ID NO 19
<211> LENGTH: 5
<212> TYPE: PRT
<213> ORGANISM: Artificial Sequence
<220> FEATURE:
<223> OTHER INFORMATION: CDR1 of VH of EnL4

<400> SEQUENCE: 19

Ser Phe Tyr Met Phe
1               5

<210> SEQ ID NO 20
<211> LENGTH: 5
<212> TYPE: PRT
<213> ORGANISM: Artificial Sequence
<220> FEATURE:
<223> OTHER INFORMATION: CDR1 of VH of EnL5

<400> SEQUENCE: 20

Ser Tyr Ala Met His
1               5
```

```
<210> SEQ ID NO 21
<211> LENGTH: 17
<212> TYPE: PRT
<213> ORGANISM: Artificial Sequence
<220> FEATURE:
<223> OTHER INFORMATION: CDR2 of VH of EnL1

<400> SEQUENCE: 21

Gly Ile Asn Asn Ala Gly Ser Thr Thr Asn His Gly Ala Ala Val Lys
1               5                   10                  15
Gly

<210> SEQ ID NO 22
<211> LENGTH: 18
<212> TYPE: PRT
<213> ORGANISM: Artificial Sequence
<220> FEATURE:
<223> OTHER INFORMATION: CDR2 of VH of EnL2

<400> SEQUENCE: 22

Gly Ile Glu Asn Ala Ala Gly Ile Gly Thr Phe Tyr Gly Ala Ala Val
1               5                   10                  15
Lys Gly

<210> SEQ ID NO 23
<211> LENGTH: 17
<212> TYPE: PRT
<213> ORGANISM: Artificial Sequence
<220> FEATURE:
<223> OTHER INFORMATION: CDR2 of VH of EnL3

<400> SEQUENCE: 23

Ala Ile Ser Asn Thr Gly Arg Tyr Thr Gly Tyr Gly Ser Ala Val Lys
1               5                   10                  15
Gly

<210> SEQ ID NO 24
<211> LENGTH: 17
<212> TYPE: PRT
<213> ORGANISM: Artificial Sequence
<220> FEATURE:
<223> OTHER INFORMATION: CDR2 of VH of EnL4

<400> SEQUENCE: 24

Gly Ile Ser Gly Asp Gly Arg Tyr Thr Gly Tyr Gly Ala Ala Val Asp
1               5                   10                  15
Gly

<210> SEQ ID NO 25
<211> LENGTH: 19
<212> TYPE: PRT
<213> ORGANISM: Artificial Sequence
<220> FEATURE:
<223> OTHER INFORMATION: CDR2 of VH of EnL5

<400> SEQUENCE: 25

Gly Ile Ser Arg Asp Gly Gly Ser Ser Thr Arg Tyr Tyr Gly Ala Ala
1               5                   10                  15
Val Lys Gly

<210> SEQ ID NO 26
<211> LENGTH: 10
<212> TYPE: PRT
```

```
<213> ORGANISM: Artificial Sequence
<220> FEATURE:
<223> OTHER INFORMATION: CDR3 of VH of EnL1

<400> SEQUENCE: 26

Ser Pro Gly Gly Ile Asp Gly Ile Asp Gly
1               5                   10

<210> SEQ ID NO 27
<211> LENGTH: 14
<212> TYPE: PRT
<213> ORGANISM: Artificial Sequence
<220> FEATURE:
<223> OTHER INFORMATION: CDR3 of VH of EnL2

<400> SEQUENCE: 27

Gly Ala Asp Thr Gly Gly Trp Pro Ala Ala Asn Ile Asp Ala
1               5                   10

<210> SEQ ID NO 28
<211> LENGTH: 14
<212> TYPE: PRT
<213> ORGANISM: Artificial Sequence
<220> FEATURE:
<223> OTHER INFORMATION: CDR3 of VH of EnL3

<400> SEQUENCE: 28

Asp Gly Cys Ala Gly Cys Cys Gly Ser Tyr Tyr Ile Asp Gly
1               5                   10

<210> SEQ ID NO 29
<211> LENGTH: 14
<212> TYPE: PRT
<213> ORGANISM: Artificial Sequence
<220> FEATURE:
<223> OTHER INFORMATION: CDR3 of VH of EnL4

<400> SEQUENCE: 29

Glu Ser Gly Ser Gly Cys Cys Asn Gly Asp Asn Ile Asp Ala
1               5                   10

<210> SEQ ID NO 30
<211> LENGTH: 14
<212> TYPE: PRT
<213> ORGANISM: Artificial Sequence
<220> FEATURE:
<223> OTHER INFORMATION: CDR3 of VH of EnL5

<400> SEQUENCE: 30

Asp Ser Asp Asn Gly Gly Tyr Tyr Cys Asp Asp Ile Asp Ala
1               5                   10

<210> SEQ ID NO 31
<211> LENGTH: 102
<212> TYPE: PRT
<213> ORGANISM: Artificial Sequence
<220> FEATURE:
<223> OTHER INFORMATION: amino acid of EnL1

<400> SEQUENCE: 31

Ala Leu Thr Gln Pro Ser Ser Val Ser Ala Asn Pro Gly Gly Thr Val
1               5                   10                  15

Glu Ile Thr Cys Ser Gly Gly Ser Gly Ser Tyr Gly Trp Phe Gln Gln
                20                  25                  30

Lys Ala Pro Gly Ser Ala Pro Val Thr Pro Ile Tyr Ala Asn Thr Asn
        35                  40                  45
```

Arg Pro Ser Asp Ile Pro Ser Arg Phe Ser Gly Ser Lys Ser Gly Ser
    50                  55                  60

Thr Ala Thr Leu Thr Ile Thr Gly Val Gln Ala Asp Asp Glu Ala Val
65                  70                  75                  80

Tyr Phe Cys Gly Gly Tyr Asp Ser Ser Ala Gly Ile Phe Gly Ala Gly
                85                  90                  95

Thr Thr Leu Thr Val Leu
            100

<210> SEQ ID NO 32
<211> LENGTH: 104
<212> TYPE: PRT
<213> ORGANISM: Artificial Sequence
<220> FEATURE:
<223> OTHER INFORMATION: amino acid of VL of EnL2

<400> SEQUENCE: 32

Ala Leu Thr Gln Pro Ser Ser Val Ser Ala Asn Pro Gly Gly Thr Val
1               5                   10                  15

Glu Ile Thr Cys Ser Gly Gly Ser Ser Tyr Gly Tyr Gly Trp Tyr
                20                  25                  30

Gln Gln Lys Ser Pro Gly Ser Pro Val Thr Val Ile Tyr Asn Asp
            35                  40                  45

Asn Gln Arg Pro Ser Asp Ile Pro Ser Arg Phe Ser Gly Ala Leu Ser
    50                  55                  60

Gly Ser Thr Ala Thr Leu Thr Ile Thr Gly Val Gln Ala Asp Asp Glu
65                  70                  75                  80

Ala Val Tyr Phe Cys Gly Ser Gly Asp Ser Ser Thr Gly Met Phe Gly
                85                  90                  95

Ala Gly Thr Thr Leu Thr Val Leu
            100

<210> SEQ ID NO 33
<211> LENGTH: 104
<212> TYPE: PRT
<213> ORGANISM: Artificial Sequence
<220> FEATURE:
<223> OTHER INFORMATION: amino acid of VL of EnL3

<400> SEQUENCE: 33

Ala Leu Thr Gln Pro Ser Ser Val Ser Ala Asn Pro Gly Gly Thr Val
1               5                   10                  15

Glu Ile Thr Cys Ser Gly Ser Ser Gly Ser Tyr Gly Trp Tyr Gln Gln
                20                  25                  30

Lys Ser Pro Gly Ser Ala Pro Val Thr Val Ile Tyr Arg Asp Asp Lys
            35                  40                  45

Arg Pro Ser Asp Ile Pro Ser Arg Phe Ser Gly Ser Leu Ser Gly Ser
    50                  55                  60

Thr Ala Thr Leu Thr Ile Thr Gly Val Gln Ala Glu Asp Glu Ala Val
65                  70                  75                  80

Tyr Phe Tyr Gly Ser Gly Glu Ser Ser Thr Asn Asn Gly Ile Phe Gly
                85                  90                  95

Ala Gly Thr Thr Leu Thr Val Leu
            100

<210> SEQ ID NO 34
<211> LENGTH: 105
<212> TYPE: PRT
<213> ORGANISM: Artificial Sequence
<220> FEATURE:

<223> OTHER INFORMATION: amino acid of VL of EnL4

<400> SEQUENCE: 34

Ala Leu Thr Gln Pro Ser Ser Val Ser Ala Asn Pro Gly Gly Thr Val
1               5                   10                  15

Glu Ile Thr Cys Ser Gly Ser Ser Tyr Gly Tyr Ser Arg His
            20                  25                  30

Gln Gln Lys Ser Pro Gly Ser Ala Pro Val Thr Ala Ile Tyr Ser Asn
        35                  40                  45

Asn Gln Arg Pro Ser Asp Ile Pro Ser Arg Phe Ser Gly Ser Thr Ser
    50                  55                  60

Gly Ser Thr Ala Thr Leu Thr Ile Thr Gly Val Gln Ala Asp Asp Glu
65                  70                  75                  80

Ala Val Tyr Phe Cys Gly Ser Met Asp Ser Ser Asn Ser Gly Val Phe
                85                  90                  95

Gly Ala Gly Thr Thr Leu Thr Val Leu
            100                 105

<210> SEQ ID NO 35
<211> LENGTH: 106
<212> TYPE: PRT
<213> ORGANISM: Artificial Sequence
<220> FEATURE:
<223> OTHER INFORMATION: amino acid of VL of EnL5

<400> SEQUENCE: 35

Ala Leu Thr Gln Pro Ser Ser Val Ser Ala Asn Pro Gly Gly Thr Val
1               5                   10                  15

Glu Ile Thr Cys Ser Gly Ser Ser Gly Tyr Gly Tyr Gly Trp Tyr Gln
            20                  25                  30

Gln Lys Ser Pro Gly Ser Ala Pro Val Thr Val Ile Tyr Ser Asn Asp
        35                  40                  45

Lys Arg Pro Ser Asp Ile Pro Ser Arg Phe Ser Gly Ser Ala Ser Gly
    50                  55                  60

Ser Thr Ala Thr Leu Thr Ile Thr Gly Val Arg Ala Glu Asp Glu Ala
65                  70                  75                  80

Val Tyr Phe Cys Gly Gly Tyr Asp Ser Ser Ala Ser Tyr Val Gly Ile
                85                  90                  95

Phe Gly Ala Gly Thr Thr Leu Thr Val Leu
            100                 105

<210> SEQ ID NO 36
<211> LENGTH: 144
<212> TYPE: PRT
<213> ORGANISM: Artificial Sequence
<220> FEATURE:
<223> OTHER INFORMATION: amino acid of VH of EnL1

<400> SEQUENCE: 36

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Gly Ile Asn Asn Ala Gly Ser Thr Thr Asn His Gly Ala Ala Val
    50                  55                  60

Lys Gly Arg Ala Thr Ile Ser Arg Asp Asn Gly Gln Ser Thr Leu Arg
65                  70                  75                  80

```
Leu Gln Leu Asn Asp Leu Arg Ala Glu Asp Thr Gly Thr Tyr Tyr Cys
                85                  90                  95

Ala Arg Ser Pro Gly Gly Ile Asp Gly Ile Asp Gly Trp Gly His Gly
            100                 105                 110

Thr Glu Val Ile Val Ser Ser Thr Ser Gly Gln Ala Gly Gln His His
        115                 120                 125

His His His His Gly Ala Tyr Pro Tyr Asp Val Pro Asp Tyr Ala Ser
    130                 135                 140
```

<210> SEQ ID NO 37
<211> LENGTH: 149
<212> TYPE: PRT
<213> ORGANISM: Artificial Sequence
<220> FEATURE:
<223> OTHER INFORMATION: amino acid of VH of EnL2

<400> SEQUENCE: 37

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Asp Phe Ser Ser His
            20                  25                  30

Asp Met Gly Trp Val Arg Gln Ala Pro Gly Lys Gly Leu Glu Phe Val
        35                  40                  45

Ala Gly Ile Glu Asn Ala Ala Gly Ile Gly Thr Phe Tyr Gly Ala Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Pro Glu Asp Thr Gly Thr Tyr Phe
                85                  90                  95

Cys Ala Arg Gly Ala Asp Thr Gly Gly Trp Pro Ala Ala Asn Ile Asp
            100                 105                 110

Ala Trp Gly His Gly Thr Glu Val Ile Val Ser Ser Thr Ser Gly Gln
        115                 120                 125

Ala Gly Gln His His His His His His Gly Ala Tyr Pro Tyr Asp Val
    130                 135                 140

Pro Asp Tyr Ala Ser
145
```

<210> SEQ ID NO 38
<211> LENGTH: 148
<212> TYPE: PRT
<213> ORGANISM: Artificial Sequence
<220> FEATURE:
<223> OTHER INFORMATION: amino acid of VH of EnL3

<400> SEQUENCE: 38

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ala Leu Thr Asp Tyr
            20                  25                  30

Cys Val Gln Trp Val Arg Gln Ala Pro Gly Lys Gly Leu Glu Phe Val
        35                  40                  45

Ala Ala Ile Ser Asn Thr Gly Arg Tyr Thr Gly Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Val Asn Asn Leu Arg Ala Glu Asp Met Gly Thr Tyr Phe Cys
                85                  90                  95
```

```
Thr Arg Asp Gly Cys Ala Gly Cys Cys Gly Ser Tyr Tyr Ile Asp Gly
            100                 105                 110

Trp Gly His Gly Thr Glu Val Ile Val Ser Ser Thr Ser Gly Gln Ala
            115                 120                 125

Gly Gln His His His His His Gly Ala Tyr Pro Tyr Asp Val Pro
        130                 135                 140

Asp Tyr Ala Ser
145

<210> SEQ ID NO 39
<211> LENGTH: 148
<212> TYPE: PRT
<213> ORGANISM: Artificial Sequence
<220> FEATURE:
<223> OTHER INFORMATION: amino acid of VH of EnL4

<400> SEQUENCE: 39

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Tyr Met Phe Trp Val Arg Gln Ala Pro Gly Lys Gly Leu Glu Trp Val
        35                  40                  45

Ala Gly Ile Ser Gly Asp Gly Arg Tyr Thr Gly Tyr Gly Ala Ala Val
50                  55                  60

Asp Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Ile Tyr Tyr Cys
            85                  90                  95

Ala Arg Glu Ser Gly Ser Gly Cys Cys Asn Gly Asp Asn Ile Asp Ala
            100                 105                 110

Trp Gly His Gly Thr Glu Val Ile Val Ser Ser Thr Ser Gly Gln Ala
            115                 120                 125

Gly Gln His His His His His Gly Ala Tyr Pro Tyr Asp Val Pro
        130                 135                 140

Asp Tyr Ala Ser
145

<210> SEQ ID NO 40
<211> LENGTH: 150
<212> TYPE: PRT
<213> ORGANISM: Artificial Sequence
<220> FEATURE:
<223> OTHER INFORMATION: amino acid of VH of EnL5

<400> SEQUENCE: 40

Ala Val Thr Leu Asp Glu Ser Gly Gly Gly Leu Gln Thr Pro Gly Gly
1               5                   10                  15

Ala Leu Ser Leu Val Cys Lys Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Gly Ile Ser Arg Asp Gly Ser Ser Thr Arg Tyr Tyr Gly Ala
50                  55                  60

Ala Val Lys Gly Arg Ala Thr Ile Ser Arg Asp Asn Gly Gln Ser Ala
65                  70                  75                  80

Met Arg Leu Gln Leu Asn Asn Leu Arg Ala Glu Asp Thr Ala Thr Tyr
            85                  90                  95
```

```
Phe Cys Ala Lys Asp Ser Asp Asn Gly Gly Tyr Tyr Cys Asp Ile
                100                 105                 110

Asp Ala Trp Gly His Gly Thr Glu Val Ile Val Ser Ser Thr Ser Gly
        115                 120                 125

Gln Ala Gly Gln His His His His His His Gly Ala Tyr Pro Tyr Asp
    130                 135                 140

Val Pro Asp Tyr Ala Ser
145                 150

<210> SEQ ID NO 41
<211> LENGTH: 33
<212> TYPE: DNA
<213> ORGANISM: Artificial Sequence
<220> FEATURE:
<223> OTHER INFORMATION: primer sequence

<400> SEQUENCE: 41
ggtggaattc tatctattct caagatccat gcc                             33

<210> SEQ ID NO 42
<211> LENGTH: 30
<212> TYPE: DNA
<213> ORGANISM: Artificial Sequence
<220> FEATURE:
<223> OTHER INFORMATION: primer sequence-reverse

<400> SEQUENCE: 42
actccatggt tacttggcca aggggtttct                                 30

<210> SEQ ID NO 43
<211> LENGTH: 39
<212> TYPE: DNA
<213> ORGANISM: Artificial Sequence
<220> FEATURE:
<223> OTHER INFORMATION: primer sequence -forward

<400> SEQUENCE: 43
ccgcgtgaat tcggggatcc atgtctattc tcaagatcc                       39

<210> SEQ ID NO 44
<211> LENGTH: 37
<212> TYPE: DNA
<213> ORGANISM: Artificial Sequence
<220> FEATURE:
<223> OTHER INFORMATION: primer sequence-reverse

<400> SEQUENCE: 44
catggagtcg acctcgagct tggccaaggg gtttctg                         37

<210> SEQ ID NO 45
<211> LENGTH: 7
<212> TYPE: PRT
<213> ORGANISM: Artificial Sequence
<220> FEATURE:
<223> OTHER INFORMATION: Synthic sequence

<400> SEQUENCE: 45

Gly Gly Ser Ser Arg Ser Ser
1               5

<210> SEQ ID NO 46
<211> LENGTH: 18
<212> TYPE: DNA
<213> ORGANISM: Artificial Sequence
<220> FEATURE:
```

<223> OTHER INFORMATION: primer sequence

<400> SEQUENCE: 46 ggssrsssssg gggsgggg                                                    18

<210> SEQ ID NO 47
<211> LENGTH: 24
<212> TYPE: DNA
<213> ORGANISM: Artificial Sequence
<220> FEATURE:
<223> OTHER INFORMATION: primer sequence

<400> SEQUENCE: 47
aagacagcta tcgcgattgc agtg                                              24

<210> SEQ ID NO 48
<211> LENGTH: 21
<212> TYPE: DNA
<213> ORGANISM: Artificial Sequence
<220> FEATURE:
<223> OTHER INFORMATION: primer sequence

<400> SEQUENCE: 48
ggtggttcct ctagatcttc c                                                 21

<210> SEQ ID NO 49
<211> LENGTH: 104
<212> TYPE: PRT
<213> ORGANISM: Artificial Sequence
<220> FEATURE:
<223> OTHER INFORMATION: germline VL

<400> SEQUENCE: 49

Ala Leu Thr Gln Pro Ser Ser Val Ser Ala Asn Pro Gly Gly Thr Val
1               5                   10                  15

Lys Ile Thr Cys Ser Gly Asp Ser Ser Tyr Tyr Gly Trp Tyr Gln Gln
            20                  25                  30

Lys Ala Pro Gly Ser Ala Pro Val Thr Val Ile Tyr Asp Asn Thr Asn
        35                  40                  45

Arg Pro Ser Asn Ile Pro Ser Arg Phe Ser Gly Ser Lys Ser Gly Ser
    50                  55                  60

Thr Ala Thr Leu Thr Ile Thr Gly Val Arg Ala Asp Asp Asn Ala Val
65                  70                  75                  80

Tyr Tyr Cys Ala Ser Thr Asp Ser Ser Ser Thr Ala Gly Ile Phe Gly
                85                  90                  95

Ala Gly Thr Thr Leu Thr Val Leu
            100

<210> SEQ ID NO 50
<211> LENGTH: 142
<212> TYPE: PRT
<213> ORGANISM: Artificial Sequence
<220> FEATURE:
<223> OTHER INFORMATION: amino acid sequence of germline VH

<400> SEQUENCE: 50

Ala Val Thr Leu Asp Glu Ser Gly Gly Gly Leu Gln Thr Pro Gly Gly
1               5                   10                  15

Ala Leu Arg Leu Val Cys Lys Ala Ser Gly Phe Thr Phe Ser Ser Tyr
            20                  25                  30

Asp Met Leu Trp Val Arg Gln Ala Pro Gly Lys Gly Leu Glu Phe Val
        35                  40                  45

```
Ala Gly Ile Asp Asn Thr Gly Ser Tyr Thr His Tyr Gly Ala Ala Val
    50              55              60

Lys Gly Arg Ala Thr Ile Ser Arg Asp Asn Gly Gln Ser Thr Gly Arg
65          70              75              80

Leu Gln Leu Asn Asn Leu Arg Ala Glu Asp Thr Ala Thr Tyr Tyr Cys
            85              90              95

Ala Lys Arg Thr Ala Gly Ser Ile Asp Ala Trp Gly His Gly Thr Glu
            100             105             110

Val Ile Val Ser Ser Thr Ser Gly Gln Ala Gly Gln His His His His
        115             120             125

His His Gly Ala Tyr Pro Tyr Asp Val Pro Asp Tyr Ala Ser
    130             135             140
```